(12) United States Patent
Reynolds et al.

(10) Patent No.: US 10,073,051 B2
(45) Date of Patent: Sep. 11, 2018

(54) REPLACEABLE MULTISTRIP CARTRIDGE AND BIOSENSOR METER

(71) Applicant: Ascensia Diabetes Care Holdings AG, Basel (CH)

(72) Inventors: Jeffery S. Reynolds, New Fairfield, CT (US); Robert S. Sams, Pittsfield, MA (US); Simin Yao, Boonton Township, NJ (US); Eugene Prais, West Milford, NJ (US); Michael A. Botta, Manorville, NY (US); Steven C. Charlton, Osceola, IN (US); Mirza Kokic, New York, NY (US)

(73) Assignee: Ascensia Diabetes Care Holdings AG, Basel (CH)

( * ) Notice: Subject to any disclaimer, the term of this patent is extended or adjusted under 35 U.S.C. 154(b) by 155 days.

(21) Appl. No.: 15/175,856

(22) Filed: Jun. 7, 2016

(65) Prior Publication Data

US 2016/0290950 A1 Oct. 6, 2016

Related U.S. Application Data

(62) Division of application No. 14/403,866, filed as application No. PCT/US2013/030897 on Mar. 13, 2013, now Pat. No. 9,383,333.
(Continued)

(51) Int. Cl.
*G01N 27/327* (2006.01)
*G01N 33/487* (2006.01)
(Continued)

(52) U.S. Cl.
CPC ..... *G01N 27/3272* (2013.01); *A61B 5/14532* (2013.01); *A61B 5/151* (2013.01);
(Continued)

(58) Field of Classification Search
CPC ....... G01N 33/48757; G01N 33/48778; G01N 33/487; G01N 27/3272; G01N 27/3273;
(Continued)

(56) References Cited

U.S. PATENT DOCUMENTS 4,217,331 A 8/1980 Schaub
4,223,524 A 9/1980 Nakagawa
(Continued)

FOREIGN PATENT DOCUMENTS

EP 1321769 6/2003
EP 1726950 11/2006
(Continued)

OTHER PUBLICATIONS

European Extended Search Report of European Application No. 17198856.1 dated Nov. 27, 2017.
(Continued)

*Primary Examiner* — Gurpreet Kaur
(74) *Attorney, Agent, or Firm* — Dugan & Dugan, PC

(57) ABSTRACT

A blood glucose monitor includes a can, a replaceable sensor cartridge that includes a frame, an upper spring disposed between the frame and the can, a case for housing the can and sealing the frame, a lower spring disposed between the can and the case, and a meter housing for sealing an upper portion of the frame. The can is capable of accepting the replaceable sensor cartridge. The frame of the removable cartridge has at least at least two walls defining a chamber for accepting a plurality of biosensors, and a bottom portion defining an opening and at least one sealing flange. The frame can further include a desiccant material capable of reducing humidity within the frame. The frame may be dimensioned such that an interference fit constrains the plurality of biosensors prior to inserting the frame within a blood glucose monitor.

20 Claims, 18 Drawing Sheets

Related U.S. Application Data

(60) Provisional application No. 61/653,603, filed on May 31, 2012.

(51) Int. Cl.
*A61B 5/15* (2006.01)
*A61B 5/145* (2006.01)
*A61B 5/151* (2006.01)

(52) U.S. Cl.
CPC ... *A61B 5/150358* (2013.01); *G01N 27/3273* (2013.01); *G01N 33/48757* (2013.01); *A61B 5/150022* (2013.01); *A61B 2562/0295* (2013.01)

(58) Field of Classification Search
CPC .............. B65B 5/08; B01L 2300/0636; B01L 2300/0825
See application file for complete search history.

(56) References Cited

U.S. PATENT DOCUMENTS

| | | | |
|---|---|---|---|
| 4,328,184 | A | 5/1982 | Kondo |
| 5,120,420 | A | 6/1992 | Nankai et al. |
| 5,194,393 | A | 3/1993 | Hugl et al. |
| 5,510,266 | A | 4/1996 | Bonner et al. |
| 5,575,403 | A | 11/1996 | Charlton et al. |
| 5,630,986 | A | 5/1997 | Charlton et al. |
| 5,632,410 | A | 5/1997 | Moulton et al. |
| 5,645,798 | A | 7/1997 | Schreiber et al. |
| 5,660,791 | A | 8/1997 | Brenneman et al. |
| 5,720,924 | A | 2/1998 | Eikmeier et al. |
| 5,738,244 | A | 4/1998 | Charlton et al. |
| 5,759,364 | A | 6/1998 | Charlton et al. |
| 5,798,031 | A | 8/1998 | Charlton et al. |
| 5,810,199 | A | 9/1998 | Charlton et al. |
| 5,854,074 | A | 12/1998 | Charlton et al. |
| 5,856,195 | A | 1/1999 | Charlton et al. |
| 5,863,800 | A | 1/1999 | Eikmeier et al. |
| 6,428,664 | B1 | 8/2002 | Bhullar et al. |
| 6,478,158 | B2 | 11/2002 | Gaffney |
| 6,497,845 | B1 | 12/2002 | Sacherer |
| 6,534,017 | B1 | 3/2003 | Bottwein et al. |
| 6,827,899 | B2 | 12/2004 | Maisey et al. |
| 6,988,996 | B2 | 1/2006 | Roe et al. |
| 6,997,343 | B2 | 2/2006 | May et al. |
| 7,138,089 | B2 | 11/2006 | Aitken et al. |
| 7,198,606 | B2 | 4/2007 | Boecker |
| 7,211,096 | B2 | 5/2007 | Kuhr et al. |
| 7,264,139 | B2 | 9/2007 | Brickwood et al. |
| 7,270,247 | B2 | 9/2007 | Charlton |
| 7,364,699 | B2 | 4/2008 | Charlton |
| 7,449,148 | B2 | 11/2008 | Matsumoto et al. |
| 7,549,323 | B2 | 6/2009 | Charlton et al. |
| 7,604,592 | B2 | 10/2009 | Freeman et al. |
| 7,790,106 | B2 | 9/2010 | Uchigaki et al. |
| 7,913,838 | B2 | 3/2011 | Zhong |
| 8,105,536 | B2 | 1/2012 | Charlton |
| 8,124,014 | B2 | 2/2012 | Charlton |
| 8,158,078 | B2 | 4/2012 | Chan et al. |
| 8,296,918 | B2 | 10/2012 | Alden et al. |
| 8,372,016 | B2 | 2/2013 | Freeman et al. |
| 8,574,510 | B2 | 11/2013 | Gofman et al. |
| 9,097,700 | B2 | 8/2015 | Brown et al. |
| 9,204,829 | B2 | 12/2015 | Prais et al. |
| 2002/0057993 | A1 | 5/2002 | Maisey et al. |
| 2002/0076349 | A1 | 6/2002 | Aitken et al. |
| 2003/0223906 | A1 | 12/2003 | McAllister et al. |
| 2004/0178216 | A1 | 9/2004 | Brickwood et al. |
| 2005/0201897 | A1 | 9/2005 | Zimmer |
| 2005/0245954 | A1 | 11/2005 | Roe et al. |
| 2006/0182656 | A1 | 8/2006 | Funke et al. |
| 2007/0007183 | A1 | 1/2007 | Schulat |
| 2007/0119710 | A1 | 5/2007 | Goldberger et al. |
| 2007/0173739 | A1 | 7/2007 | Chan |
| 2007/0173740 | A1 | 7/2007 | Chan et al. |
| 2008/0093235 | A1 | 4/2008 | Zhong et al. |
| 2008/0094804 | A1 | 4/2008 | Reynolds et al. |
| 2008/0118399 | A1 | 5/2008 | Fleming |
| 2008/0131322 | A1 | 6/2008 | Kheiri et al. |
| 2008/0164164 | A1 | 7/2008 | Zhong |
| 2008/0164280 | A1 | 7/2008 | Kuriger et al. |
| 2008/0181818 | A1 | 7/2008 | Ruan |
| 2008/0190766 | A1 | 8/2008 | Rush et al. |
| 2009/0035120 | A1 | 2/2009 | List |
| 2009/0074617 | A1 | 3/2009 | Uchigaki et al. |
| 2009/0314106 | A1 | 12/2009 | Van Halsema |
| 2010/0041156 | A1 | 2/2010 | Brenneman et al. |
| 2010/0087754 | A1 | 4/2010 | Rush et al. |
| 2010/0129900 | A1 | 5/2010 | Clark et al. |
| 2010/0291568 | A1 | 11/2010 | McDevitt et al. |
| 2012/0082597 | A1 | 4/2012 | Doniger et al. |
| 2013/0048495 | A1 | 2/2013 | Charlton |
| 2013/0324822 | A1 | 12/2013 | Prais et al. |
| 2015/0004059 | A1 | 1/2015 | Brown et al. |
| 2015/0144484 | A1 | 5/2015 | Reynolds |
| 2015/0301016 | A1 | 10/2015 | Brown et al. |
| 2016/0025638 | A1 | 1/2016 | Charlton |
| 2016/0069859 | A1 | 3/2016 | Prais et al. |

FOREIGN PATENT DOCUMENTS

| | | |
|---|---|---|
| EP | 1726951 | 11/2006 |
| EP | 2426493 | 3/2012 |
| JP | S54-033797 | 3/1979 |
| JP | S56-175756 | 12/1981 |
| JP | H06-308115 | 11/1994 |
| JP | H0921811 A | 1/1997 |
| JP | 2002-310972 | 10/2002 |
| JP | 2003-028794 | 1/2003 |
| JP | 2003-302314 | 10/2003 |
| JP | 2004-4046 A | 1/2004 |
| JP | 2006-516328 | 6/2006 |
| JP | 2006-517651 | 7/2006 |
| JP | 2007-535388 | 12/2007 |
| JP | 2007-537454 | 12/2007 |
| JP | 2008-001428 | 1/2008 |
| JP | 2008-502901 | 1/2008 |
| JP | 2008-504532 | 2/2008 |
| JP | 2008-544266 | 12/2008 |
| JP | 2012-001256 | 1/2012 |
| WO | WO 95/13531 | 5/1995 |
| WO | WO 2001-023885 | 4/2001 |
| WO | WO 2002-008753 | 1/2002 |
| WO | WO 2002-018940 | 3/2002 |
| WO | WO 2003-042691 | 5/2003 |
| WO | WO 2004-063747 | 7/2004 |
| WO | WO 2005-046477 | 5/2005 |
| WO | WO 2006-002432 | 1/2006 |
| WO | WO 2006-019665 | 2/2006 |
| WO | WO 2006-044850 | 4/2006 |
| WO | WO 2006-065754 | 6/2006 |
| WO | WO 2006-076721 | 7/2006 |
| WO | WO 2007-085438 | 8/2007 |
| WO | WO 2007-147494 | 12/2007 |
| WO | WO 2008-111937 | 9/2008 |
| WO | WO 2009-120664 | 10/2009 |

OTHER PUBLICATIONS

Supplementary Partial European Search Report of European Application No. 12859868.7 dated Aug. 5, 2015.
International Search Report and Written Opinion of International Application No. PCT/US2012/070270 dated Feb. 26, 2013.
Taiwan Search Report of Taiwanese Application No. 101148835 dated Oct. 6, 2014.
International Preliminary Report on Patentability of International Application No. PCT/US2012/070270 dated Jul. 3, 2014.
International Search Report and Written Opinion of International Application No. PCT/US2014/021691 dated Sep. 10, 2014.
International Preliminary Report on Patentability of International Application No. PCT/US2014/021691 dated Sep. 24, 2015.

(56) References Cited

OTHER PUBLICATIONS

International Search Report and Written Opinion of Application No. PCT/US2012/072118 dated Mar. 28, 2013.
International Search Report and Written Opinion of Application No. PCT/US2013/030897 dated Jun. 27, 2013.
Prais et al., of U.S. Appl. No. 14/943,416, titled "Multistrip Cartridge," filed Nov. 17, 2015 (Now Published as 2016-0069859).
International Preliminary Report on Patentability of Application No. PCT/US2013/030897 dated Dec. 2, 2014.
International Preliminary Report on Patentability of Application No. PCT/US2012/072118 dated Dec. 11, 2014.
European Office Action and Search Report of European Application No. 13797254.3 dated Dec. 16, 2015.
European Extended Search Report of European Application No. EP15198651.0 dated Feb. 11, 2016.
European Extended Search Report of European Application No. 13797254.3 dated Mar. 21, 2016.
Brown et al., of U.S. Appl. No. 15/076,278, titled "Linear, Cartridge-Based Glucose Measurement System," filed Mar. 21, 2016.
Taiwan Search Report of Taiwanese Application No. 104106105 dated Aug. 8, 2016.

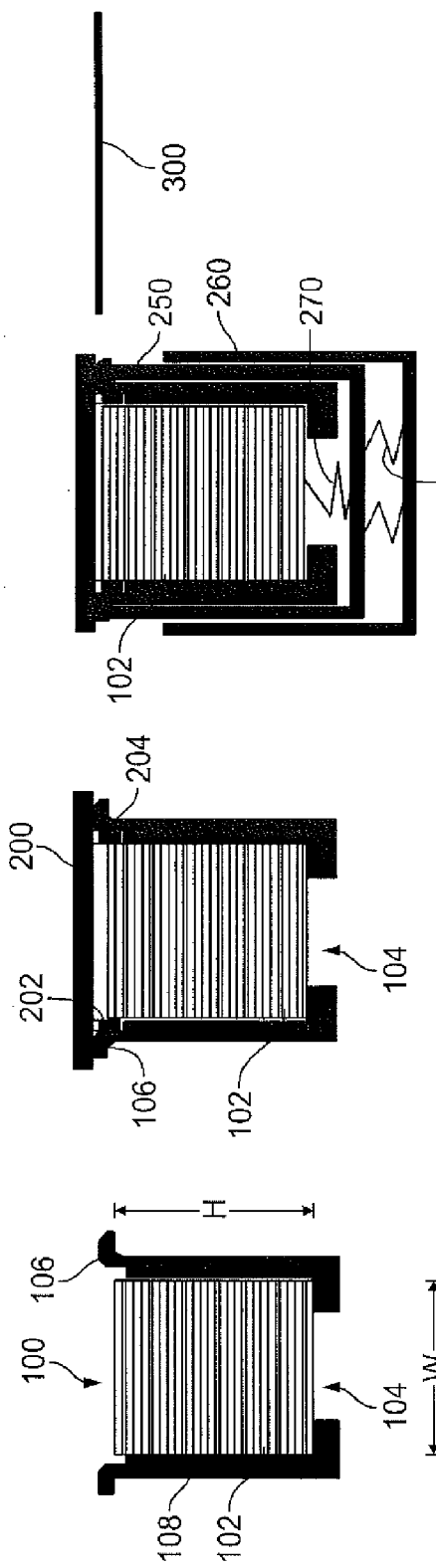
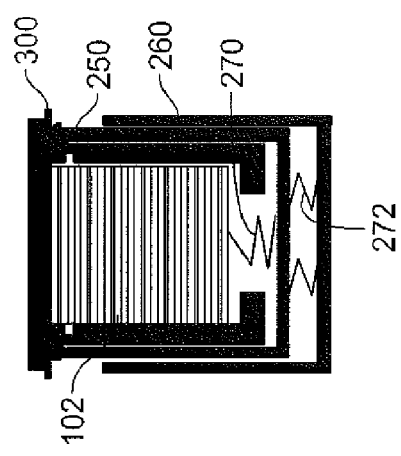
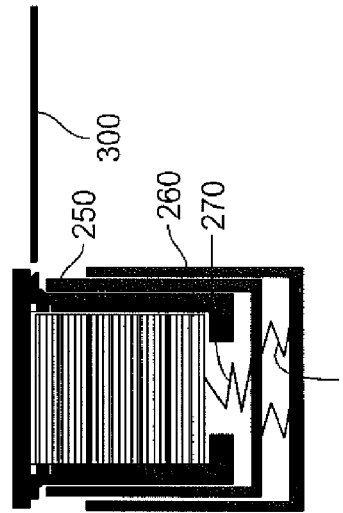
FIG. 3A  FIG. 3B  FIG. 3C  FIG. 3D  FIG. 3E

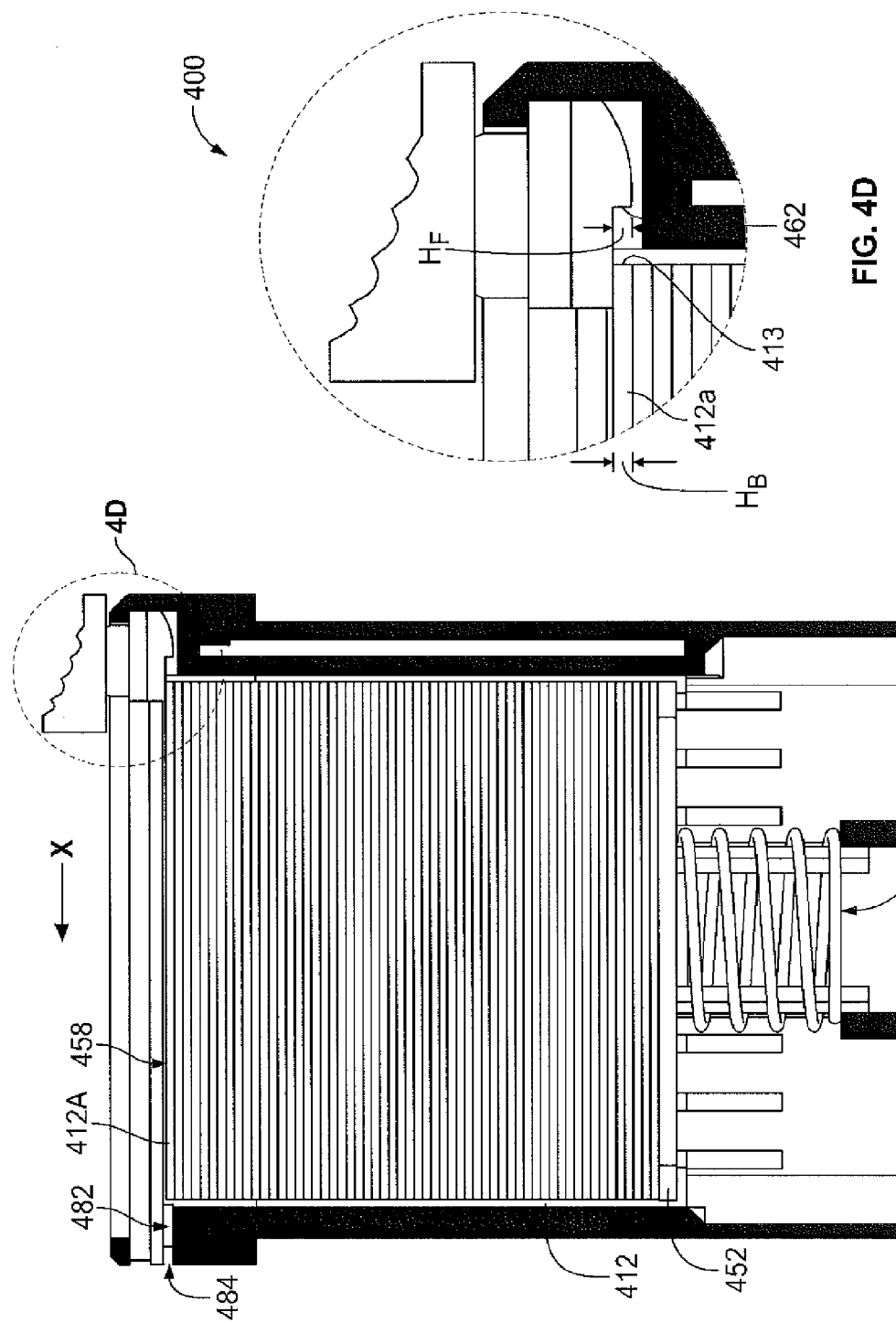

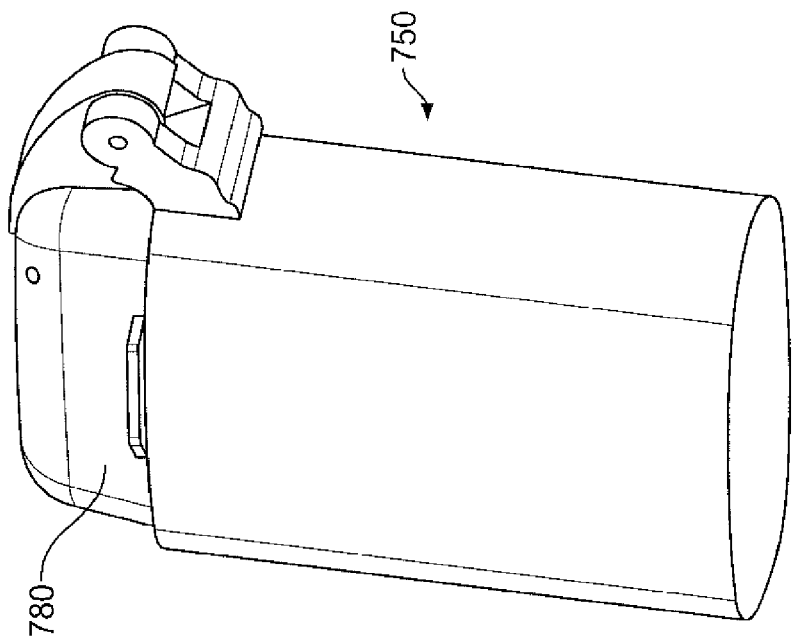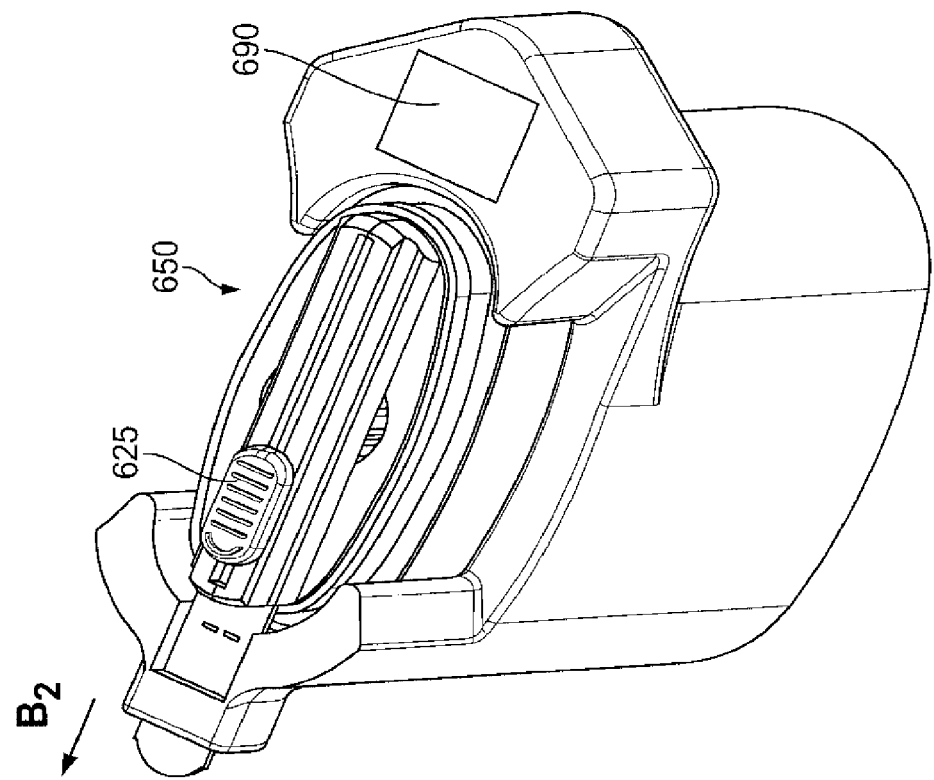

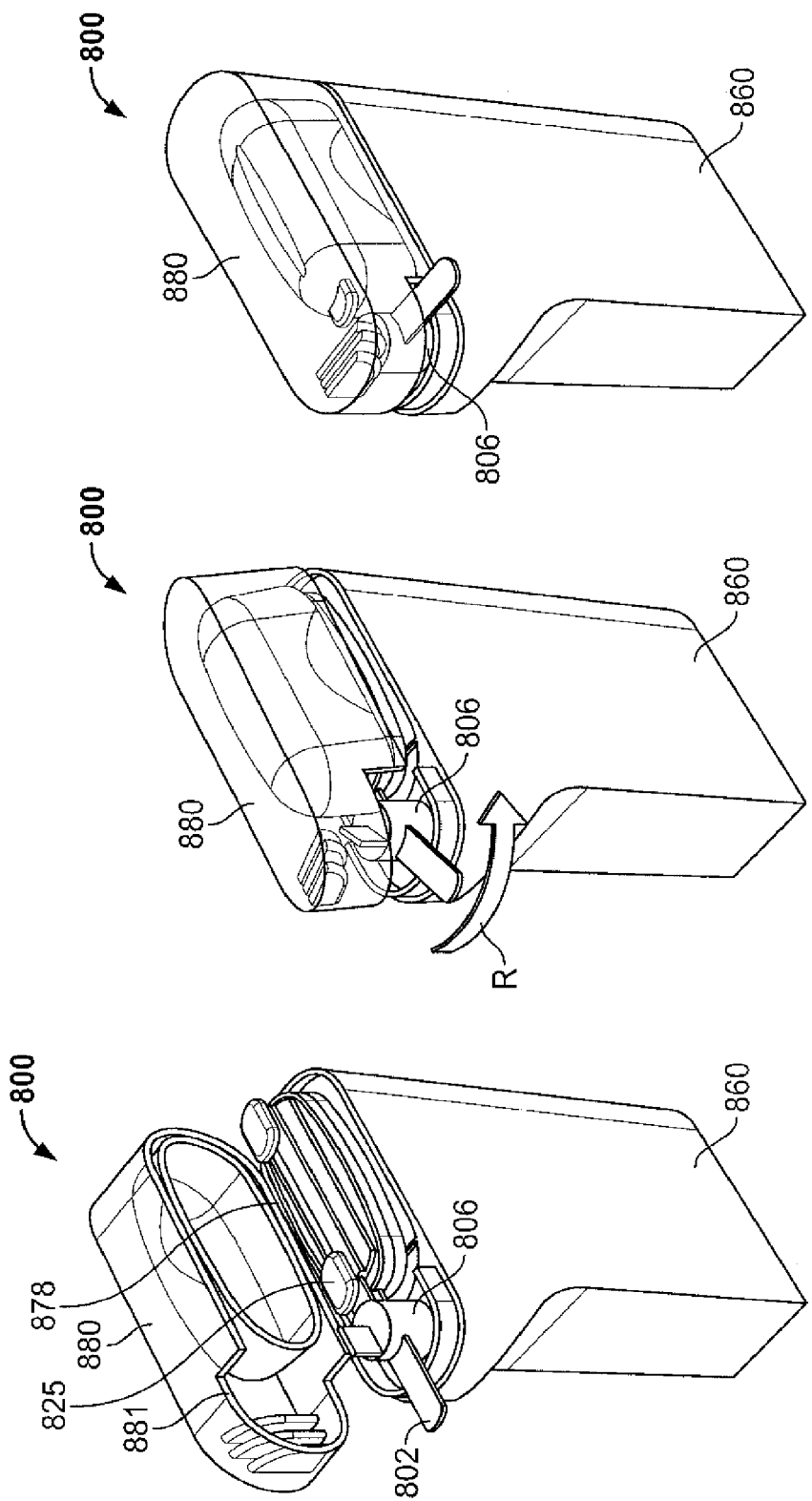

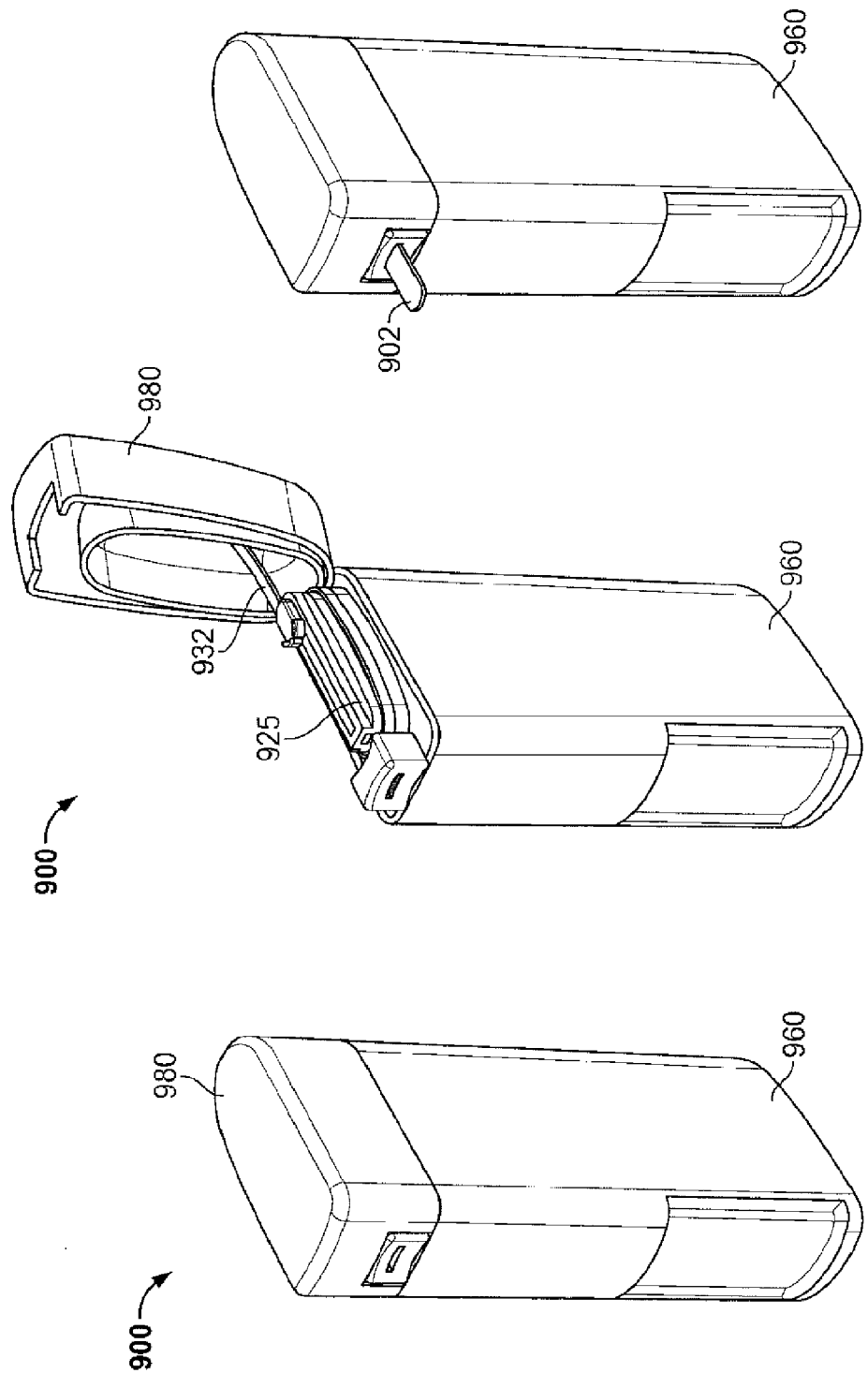

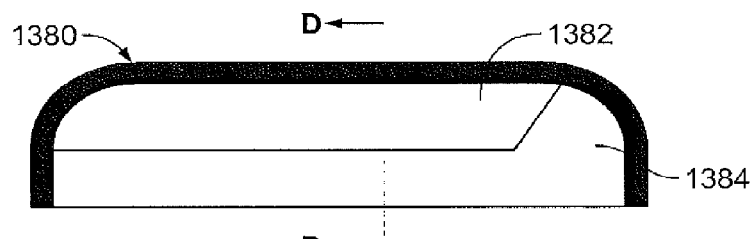
FIG. 13A
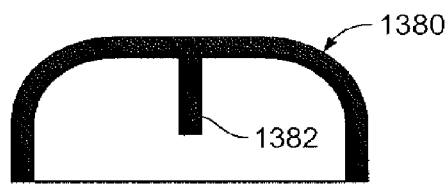
FIG. 13B
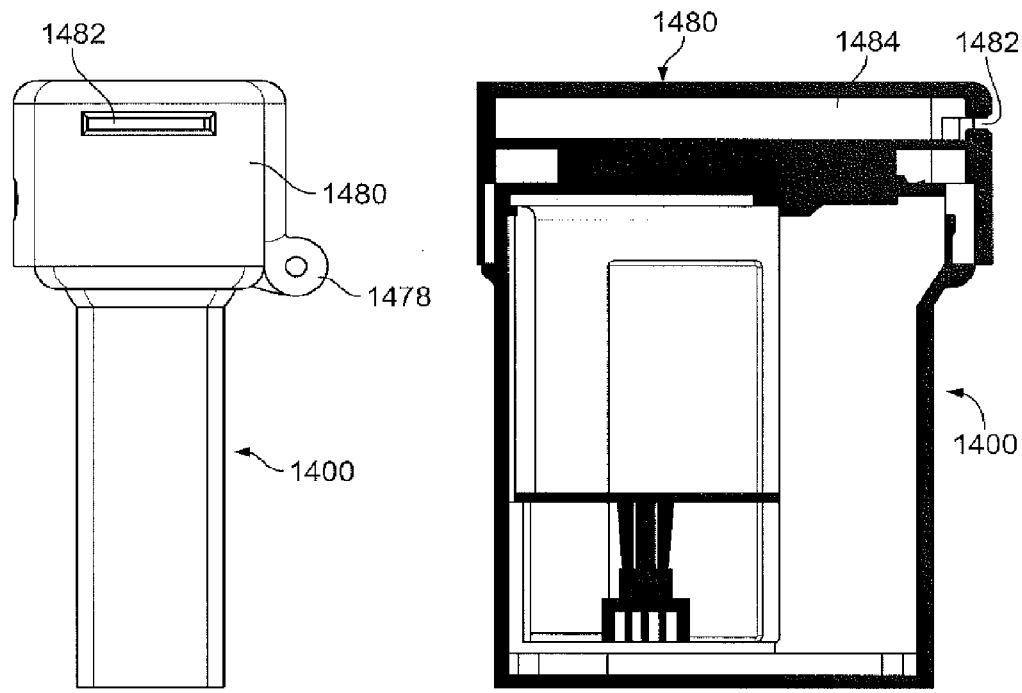
FIG. 14A
FIG. 14B

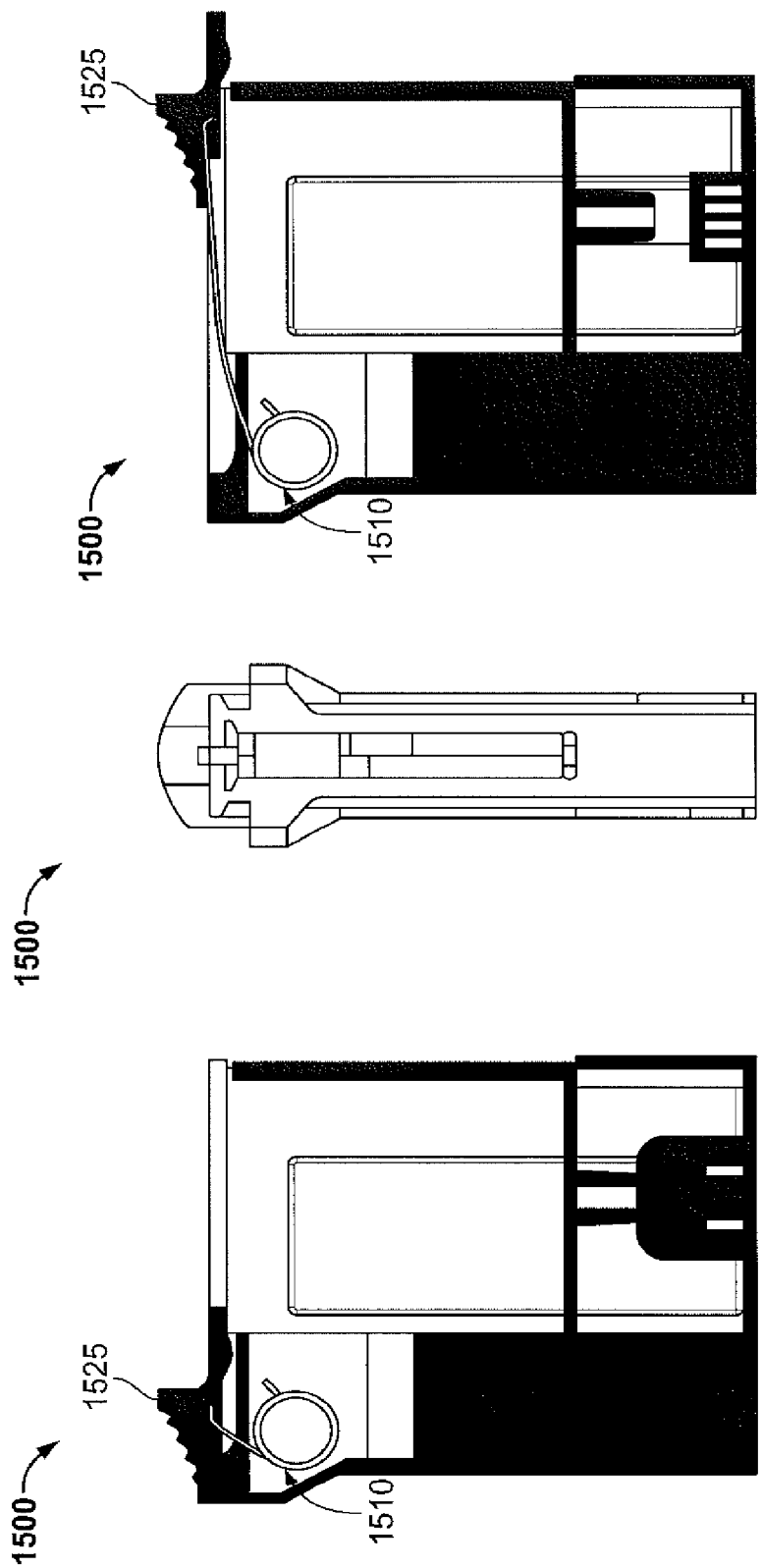

REPLACEABLE MULTISTRIP CARTRIDGE AND BIOSENSOR METER

CROSS REFERENCE TO RELATED APPLICATIONS

This is a division of U.S. patent application Ser. No. 14/403,866, filed Nov. 25, 2014, now U.S. Pat. No. 9,383,333, issued Jul. 5, 2016, which is a 371 of PCT/US2013/030897, filed Mar. 13, 2013, which claims the benefit of U.S. Prov. Patent Appln. No. 61/653,603, filed May 31, 2012, the disclosures of which are incorporated herein by reference in their entireties for all purposes.

BACKGROUND OF THE INVENTION

The present invention relates generally to blood glucose monitoring systems for determining the concentration of glucose in blood, and more particularly, to a sensor cartridge for dispensing biosensors for use with blood glucose monitoring systems.

It is often necessary to quickly obtain a sample of blood and perform an analysis of the blood sample. One example of a need for obtaining a sample of blood is in connection with a blood glucose monitoring system, which a user must frequently use to monitor the user's blood glucose level.

Those who have irregular blood glucose concentration levels are medically required to regularly self-monitor their blood glucose concentration level. An irregular blood glucose level can be brought on by a variety of reasons, including illness, such as diabetes. The purpose of monitoring the blood glucose concentration level is to determine the blood glucose concentration level and then to take corrective action, based upon whether the level is too high or too low, to bring the level back within a normal range. The failure to take corrective action can have serious implications. When blood glucose levels drop too low, a condition known as hypoglycemia, a person can become nervous, shaky and confused. That person's judgment may become impaired and that person may eventually pass out. A person can also become very ill if their blood glucose level becomes too high, a condition known as hyperglycemia. Both conditions, hypoglycemia and hyperglycemia, are potentially life-threatening emergencies.

One method of monitoring a person's blood glucose level is with a portable, hand-held blood glucose testing device. The portable nature of these devices enables the users to conveniently test their blood glucose levels wherever the user may be. The glucose testing device includes a biosensor to harvest the blood for analysis. One type of biosensor is the electrochemical biosensor. The electrochemical biosensor includes a regent designed to react with glucose in the blood to create an oxidation current at electrodes disposed within the electrochemical biosensor which is directly proportional to the user's blood glucose concentration. Such a biosensor is described in U.S. Pat. Nos. 5,120,420, 5,660,791, 5,759,364, and 5,798,031, each of which is incorporated herein in its entirety. Another type of sensor is an optical biosensor, which incorporates a reagent designed to produce a colorimetric reaction indicative of a user's blood glucose concentration level. The colorimetric reaction is then read by a spectrometer incorporated into the testing device. Such an optical biosensor is described in U.S. Pat. No. 5,194,393, which is incorporated herein by reference in its entirety.

In order to check a person's blood glucose level, a drop of blood is obtained from the person's fingertip using a lancing device, and the blood is harvested using the biosensor. The biosensor, which is inserted into a testing unit, is brought into contact with the blood drop. The biosensor draws the blood, via capillary action, inside the biosensor and the ensuing electrochemical reaction is measured by the test unit, which then determines the concentration of glucose in the blood. Once the results of the test are displayed on a display of the test unit, the biosensor is discarded. Each new test requires a new biosensor.

Referring now to FIGS. 1 and 2, examples of a testing device 10 and a package 30 of biosensors 12 ("sensor pack") are shown, respectively. The sensor pack 30 is designed to be housed within the testing device 10. Prior to each test, a collection area 14 of an individual biosensor 12 is pushed by a mechanism within the testing device 10 through its packaging and is extended from the testing device 10 through a slot 16 for harvesting a sample of blood. The testing device 10 includes a slider 18 for advancing the biosensor 12. In FIG. 1, a biosensor 12 is shown extending from the testing device 10. The collection area 14 extends from the testing device 10, while a contact area, disposed at the opposite end of the biosensor 12, shown in FIGS. 1 and 2, remains inside the testing device 10. The contact area includes terminals that electrically couple the electrodes to a meter disposed within the testing device 10 for measuring the oxidation current produced at the electrodes by the reaction of glucose and the reagent. The test unit includes a display 20.

Referring now to FIG. 2, biosensors 12 are shown disposed in the sensor pack 30. The sensor pack 30 is made up of a circular disk 32 having ten individual compartments (blisters) 34 arranged radially. The disk is made from an aluminum foil/plastic laminate which is sealed to isolate the sensor from ambient humidity and from other sensors with a burst foil cover 36. Each biosensor 12 is kept dry by a desiccant located inside a desiccant compartment 37I disposed adjacent to the compartment 34.

To retrieve a sensor, a mechanism disposed within the testing device 10, such as a knife, is driven down through the burst foil into an individual elongated compartment 34 at the end closest to the hub of the disk 32 and then moved radially toward the perimeter of the blister 34. In doing so, the knife engages the contact area 38 (fish tail) of the sensor in that compartment. Radial travel of the knife pushes the tip of the sensor out through the burst foil 36 and through parts of the testing device 10 such that the collection area 14 of the sensor 12 is completely out of the testing device 10 and ready to receive a fluid test sample such as blood. For this stage, it is essential that the bond between the base and lid of the sensor withstand the sheer forces generated when the sensor bursts out through the foil 36. This method of providing a sensor ready for use is more fully described in U.S. Pat. No. 5,575,403, which is incorporated herein by reference in its entirety.

Further details of the operational and mechanical aspects of the testing device 10 and sensor pack 30 are more fully described in U.S. Pat. Nos. 5,575,403, 5,630,986, 5,738,244, 5,810,199, 5,854,074, 5,856,195 and 8,105,536, each of which are hereby incorporated by reference in their entireties.

A drawback associated with this flat array of testing devices is the large area that is occupied. The size of testing devices that internally house such a flat array package constrains the size of the package (i.e., the number of sensors), thus making it difficult to increase the number of sensors per package. Moreover, prior art meter and cartridge assemblies include too many parts that must be replaced with each new cartridge. Finally, sensors must be handled by the user, which decreases the accuracy of the reading.

Accordingly, it would be beneficial to provide a replaceable cartridge where the replaceable portions are few and easily assembled to a meter, resulting in a lower cost of use and better accuracy in measurement.

SUMMARY OF THE INVENTION

In some embodiments, a replaceable sensor cartridge includes a frame having at least two walls defining a chamber for accepting a plurality of biosensors, the frame having a bottom portion defining a bore and a sealing flange, the frame further including a desiccant material capable of reducing humidity within the frame. The frame may be dimensioned such that an interference fit temporarily constrains the plurality of sensors prior to inserting the frame within a blood glucose monitor. Alternatively the sensors may be temporarily constrained by a thin bead of a hot-melt adhesive.

In some other embodiments a blood glucose monitor includes a can capable of accepting a replaceable sensor cartridge. An upper spring may be disposed between the frame and the can. A case for housing the can may seal the frame. A lower spring may be disposed between the can and the case. A meter housing may seal an upper portion of the frame.

In some other examples, a replaceable sensor cartridge may include a housing, a frame disposed within the housing for accepting a plurality of biosensors, and a spring for actuating the plurality of biosensors. A strip picker may be configured and arranged to slide along a top portion of the frame to deploy the top biosensor from the plurality of biosensors. The blood glucose monitor may further include an acceptance slot at the bottom of the monitor for receiving a sample placed on a biosensor. At least one electrode at the top of the housing may be configured and arranged to contact a biosensor coupled to a strip picker. Other variations may include an arm for coupling the lid to a strip picker such that movement of the lid actuates the strip picker.

BRIEF DESCRIPTION OF THE DRAWINGS

Various embodiments of the presently disclosed delivery system are disclosed herein with reference to the drawings, wherein:

FIGS. 3A-E are schematic cross-sectional views of a replaceable cartridge and its use within a meter according to one embodiment of the present invention;

FIGS. 4C and 4D are schematic cross-sectional view of the cartridge shown in FIG. 4A;

FIGS. 6A-C are perspective views of a blood glucose monitor and a sensor cartridge disposed within the monitor according to another embodiment of the present invention;

FIGS. 17A-C are perspective views of a blood glucose monitor and a sensor cartridge disposed within the monitor according to a third embodiment of the present invention;

FIGS. 8A-C are perspective views of a blood glucose monitor and a sensor cartridge disposed within the monitor according to a fourth embodiment of the present invention;

FIGS. 9A-C are perspective views of a blood glucose monitor and a sensor cartridge disposed within the monitor according to a fifth embodiment of the present invention;

FIGS. 13A and 13B are schematic cross-sectional views of a lid according to one embodiment of the present invention;

FIGS. 14A and 14B are back end and schematic cross-sectional views of a replaceable cartridge having a disposal compartment according to one embodiment of the present invention; and FIGS. 15A-C are schematic illustrations of a replaceable cartridge having a retraction spring according to one embodiment of the present invention.

Various embodiments of the present invention will now be described with reference to the appended drawings. It is appreciated that these drawings depict only some embodiments of the invention and are therefore not to be considered limiting of its scope.

DETAILED DESCRIPTION

Figure 1:
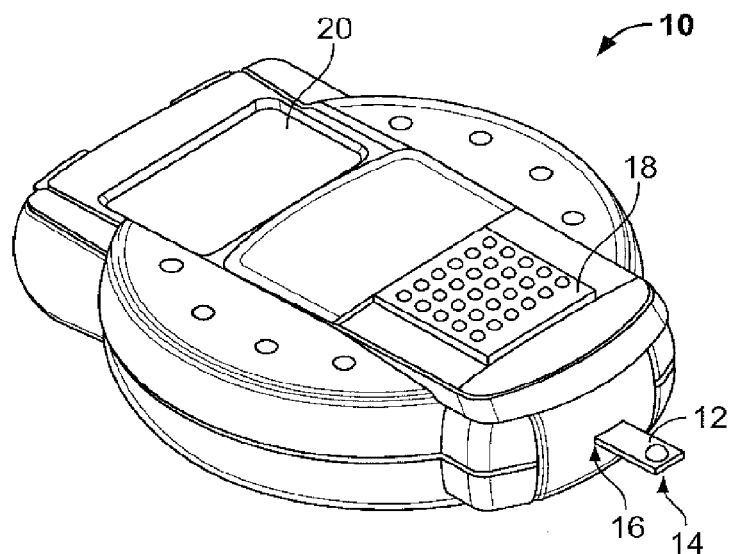
FIG. 1 is a perspective view of a prior art testing device.
Figure 2:
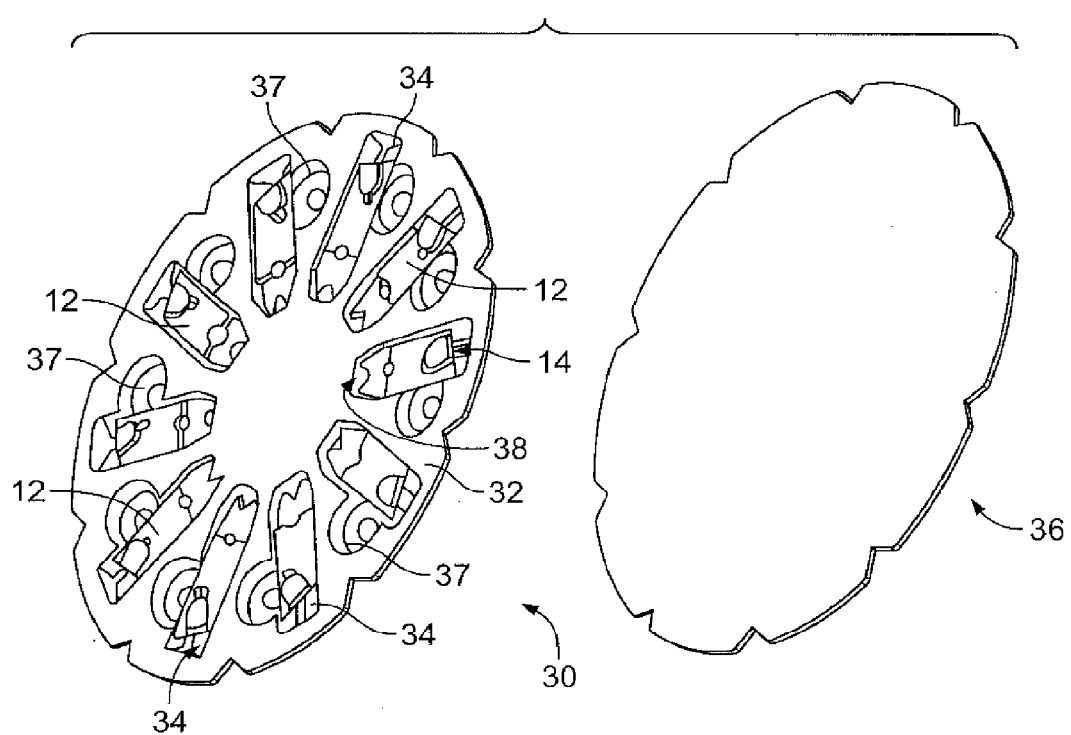
FIG. 2 is a perspective view of a prior art sensor pack having a foil lid removed.

Referring now to FIG. 3A, there is shown a sensor cartridge 100 for storing a plurality of biosensors 102, such as the biosensors 12 described in connection with FIGS. 1 and 2, according to one embodiment of the present invention. The sensor cartridge 100 provides a sealed, substantially moisture-impervious environment for storing the plurality of biosensors 102. According to one embodiment of the sensor cartridge 100, the plurality of biosensors 102 are stacked, substantially one on top of the next, as shown in FIG. 3A. In this configuration, outer edges of biosensors 102 are vertically aligned with one another. Generally, in use, the biosensors 102 are dispensed from the sensor cartridge 100 adjacent sealing flange 106. Sealing flange 106 may be formed of a single continuous radially projecting portion disposed around the circumference of desiccant material 108 or may include two or more separate portions. Supplying sensors in a cartridge is more convenient for a user when compared to a bottle. First, the cartridge provides a storage place for the sensors in a low-humidity environment and permits a smaller, less expensive sensor that, with minimal manipulation can be advanced into the meter, typically by the movement of a lever.

The stacked biosensors 102 are in vapor communication with a desiccant material 108 disposed within the sensor cartridge 100. The desiccant material 108 maintains the interior of the can 250 at an appropriate humidity level so that the reagent material disposed within the biosensors 102 is not adversely affected prior to being used. The desiccant material 108 is in the form of a small bag, round bead of material, a hot melt, a molded shape or any other form that can be readily disposed in the sensor cartridge 100. Sufficient desiccant is added to cover use-life, but not necessarily shelf-life of the package. A desiccated over-foil or other packaging may be needed for additional moisture protection. While the desiccant material 108 shown (FIG. 3A) is disposed towards a portion of the sides and bottom of the sensor cartridge 102, the desiccant material 108 may be disposed anywhere practical within the sensor cartridge 100 according to alternative embodiments of the sensor cartridge 100. The amount of such desiccant material 108 placed within the sensor cartridge 100 will be dependent on the amount that is required to maintain the interior of the sensor cartridge 100 in a desiccated state. One type of commercially available desiccant material that can be used in one embodiment of the present invention is 13× synthetic molecular sieves from Multisorb Technologies Inc. of Buffalo, N.Y., available in powder, pellet and bead forms.

The sensor cartridge 100 is made of a rigid or semi-rigid material such as plastic that forms a frame. The material may be moisture-impervious. Each of the biosensors are approximately 0.50 inch long (about 12.70 mm), approximately 0.03 inch thick (about 0.76 mm) and approximately 0.20 inch wide (about 5.08 mm). The interior of the of the sensor cartridge 100 is dimensioned only slightly larger than the length and width of the biosensors 120 to allow the biosensors 102 to move vertically within the sensor cartridge (as described below) but not side-to-side (as viewed in FIG. 3A) so that the stack of the biosensors 102 is maintained. For example, according to one embodiment of the sensor cartridge 100, the sensor cartridge 100 has an interior width W of approximately 0.52 inch (about 13.21 mm) and an interior depth (into the page as viewed in FIG. 3A) of approximately 0.22 inch (about 5.59 mm). The interior height H may be approximately 2.25 inch (about 57.15 mm) for an embodiment of the sensor cartridge that is adapted to house approximately fifty sensors. The interior height H may be varied according to alternative embodiments of the sensor cartridge 100 to accommodate an increased or decreased number of biosensor 102.

In some examples, the top opening of sensor cartridge 100 may deliberately have slightly different dimensions from biosensors 102 to cause a small amount of interference which serves to hold biosensors 102 in place during manufacture and while sensor cartridge 100 is being loaded into the meter as will be described below.

The frame of cartridge 100 may include walls to house biosensors 102. In at least some examples, the frame may include two opposing walls with two open edges therebetween. Alternatively, the frame may include three or four walls. As seen in FIG. 3A, the frame of sensor cartridge 100 may further include a bore 104 at the bottom of the cartridge. Bore 104 may be configured as any opening, lumen, slot or hole capable of accepting an actuator for pushing biosensors 102 upward. In one example, bore 104 may be configured to accept an actuator in the form of a spring (shown in FIG. 3C) as will be described in greater detail below. Bore 104 provides a channel through which biosensors 102 may be pushed up within cartridge 100. It will be understood that though FIG. 3A illustrates a single bore 104, that multiple bores 104 may be formed in the frame. Additionally, the bore 104 need not be disposed in the middle of the frame, but may be disposed at corners or edges of the frame.

Sensor cartridge 100 may be formed as described as a single unit, and packaged for individual sale. Some sensor storage bottles provide a moisture barrier, a desiccant and a seal but also require additional components related to the delivery process for the sensor such as, for example, an actuator in the form of a lift spring that is needed to push a biosensor off the top of a stacked array of sensors into a nest. Additional components in the cartridge may add to the disposable cost.

In contrast, the embodiment of sensor cartridge 100 includes only the minimum parts necessary for reliable operation of a cartridge system which is the frame (not having six sides) sufficient desiccant for the desired use-life and a seal. The remaining portions necessary for operation of a blood glucose monitor may be formed as part of a reusable meter. In this manner, the cost of the replaceable single-use sensor cartridge 100 may be reduced.

FIG. 3B illustrates sensor cartridge 100 being loaded in a meter housing 200. Meter housing 200 may include a taper fitting 204 that will contact sealing flange 106. During loading a taper fitting 204 in the meter housing 200 engages sensor cartridge 100 and deforms it in such a way as to allow biosensors 102 to move freely. Alternatively, taper fitting 204 or other fitting may be configured to depress a cartridge-latch that otherwise stops the biosensors from falling out. As seen in FIG. 3B, the assembled meter housing 200 and sensor cartridge 100 defines a segregating slot 202 that will allow individual deployment of biosensors 102. In this manner, only one biosensor 102 is deployed at a time and jamming in the assembly is reduced.

Figure 3F:
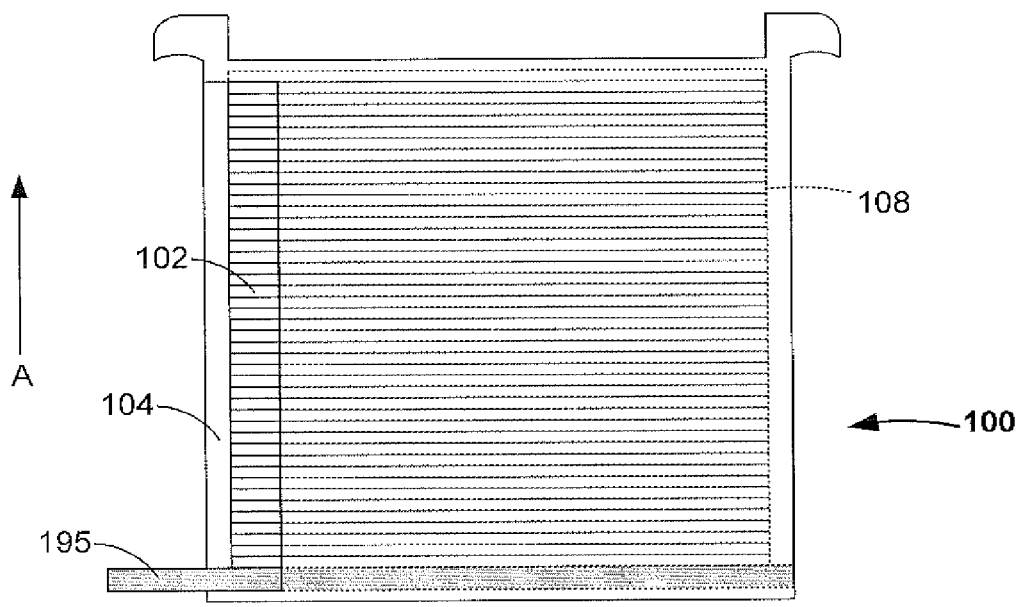
FIG. 3F is a schematic cross-sectional view of another example of a replaceable cartridge having a lift platform according to another embodiment of the present invention.

A can 250 and case 260 may be coupled to the meter housing 200 as seen in FIG. 3C. A water-impermeable can 250 may be disposed within a meter case 260 and configured to be capable of sliding within case 260. Can 250, case 260 or both may be configured to include a stop mechanism so that can 250 does not decouple from case 260. An actuator in the form of an upper spring 270 may be disposed within can 250 and passed through bore 104 of sensor cartridge 100 to actuate biosensors 102. A pair of lower springs 272 may be disposed between can 250 and case 260. As cartridge 100 is pushed into can 250 and case 260, upper spring 270 pushes biosensors 102 up to the delivery surface of the meter housing 200. Lower spring 272 in combination with case 260 forces can 250 against sealing flange 106 and housing 200 to create a sealed environment within can 250. Lower spring 272 in case 250 pushes the can onto sealing flange 106, which is trapped between the can 250 and meter housing 200, sealing biosensors 102 in a desiccated environment. In one example, the spring force of lower spring 272 may be higher than that of upper spring 270 to hold can 250, flange 106 and housing 200 together in a sealed configuration. This is the rest, or storage position of the assembly. It will be understood that upper springs 270 and lower springs 272 may each include a single spring, or multiple springs having the same or varying spring constants. In addition to upper and lower springs, the actuator may include other components for translating biosensors 102 upward toward a feed mechanism so that the biosensors may be used. For example, the actuator may include a manual lift platform 195 disposed under the lowermost biosensor 102, and projecting out of a bore 104 in the side of cartridge 100 as shown in FIG. 3F. The lift platform may be manually pushed upward to move the biosensors 102 toward the feed mechanism. The actuator may include other biased or unbiased components to translate the biosensors.

As seen in FIGS. 3C-3E a pusher 300 may be used to advance a single biosensor 102 out of sensor cartridge 100. As shown in FIG. 3D, as pusher 300 approaches, can 250 is slightly pushed downward, relieving pressure from sealing flange 106 of the cartridge 100. As pusher 300 advances further, as shown in FIG. 3D, the pusher contacts the chamfered edge of the seal and lifts the can out of the way. Segregating slot 202 ensures that just one biosensor 102 is delivered by pusher 300 at a time.

Figure 4B:
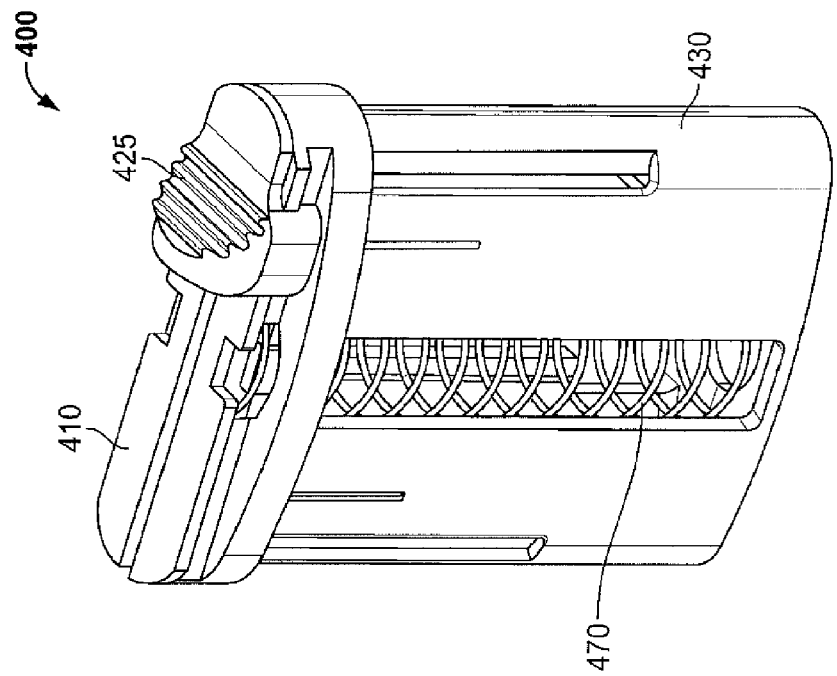
FIGS. 4A and 4B are perspective views of a sensor cartridge having a picker according to one embodiment of the present invention.
Figure 4A:
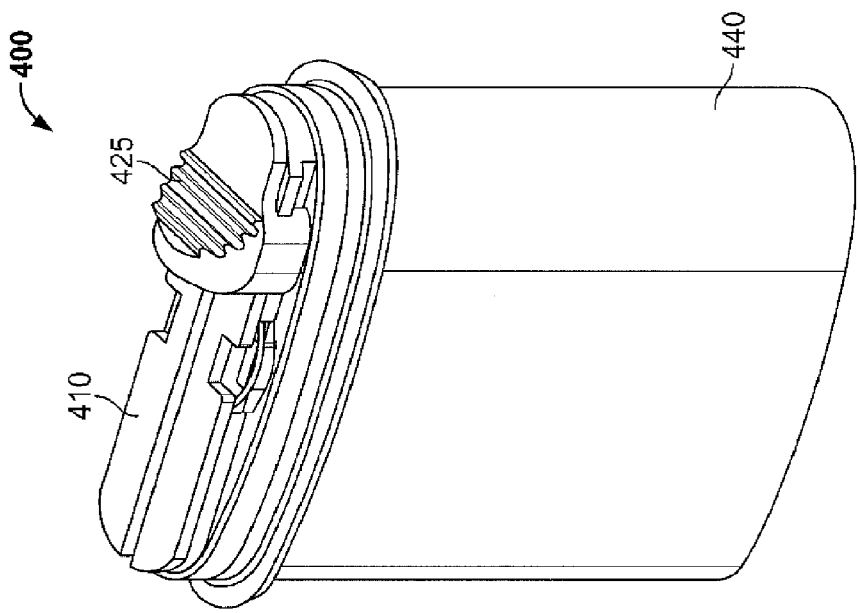
Figure 5B:
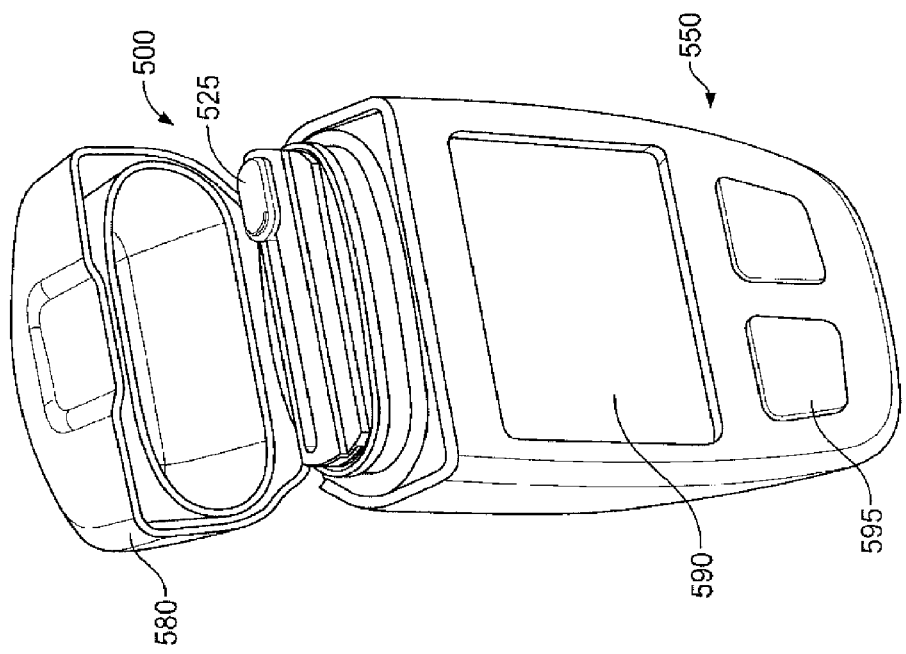
FIGS. 5A-D are perspective views of a blood glucose monitor and a sensor cartridge disposed within the monitor according to one embodiment of the present invention.
Figure 5A:
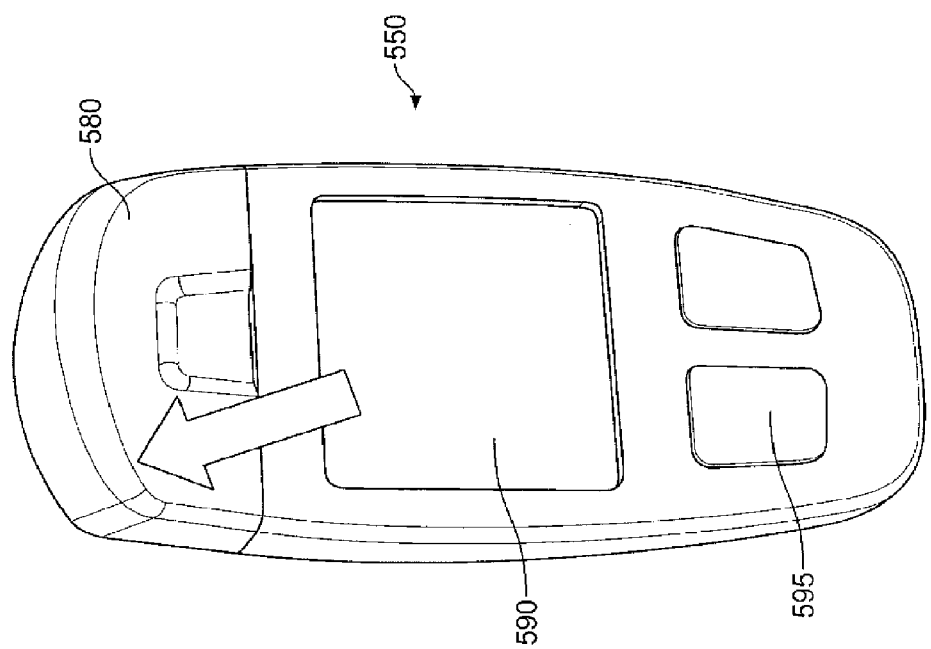
Figure 5D:
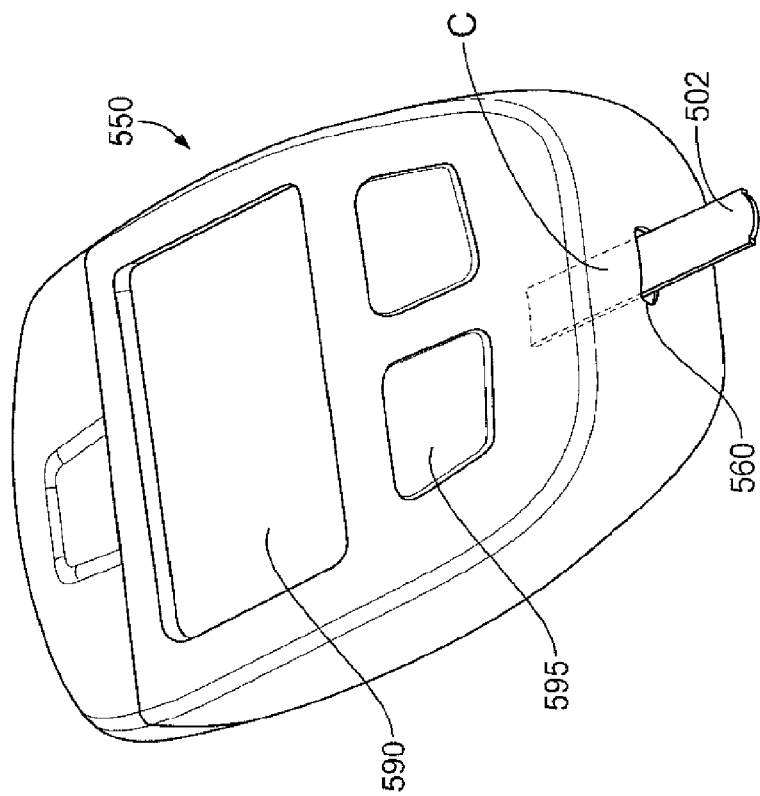
Figure 5C:
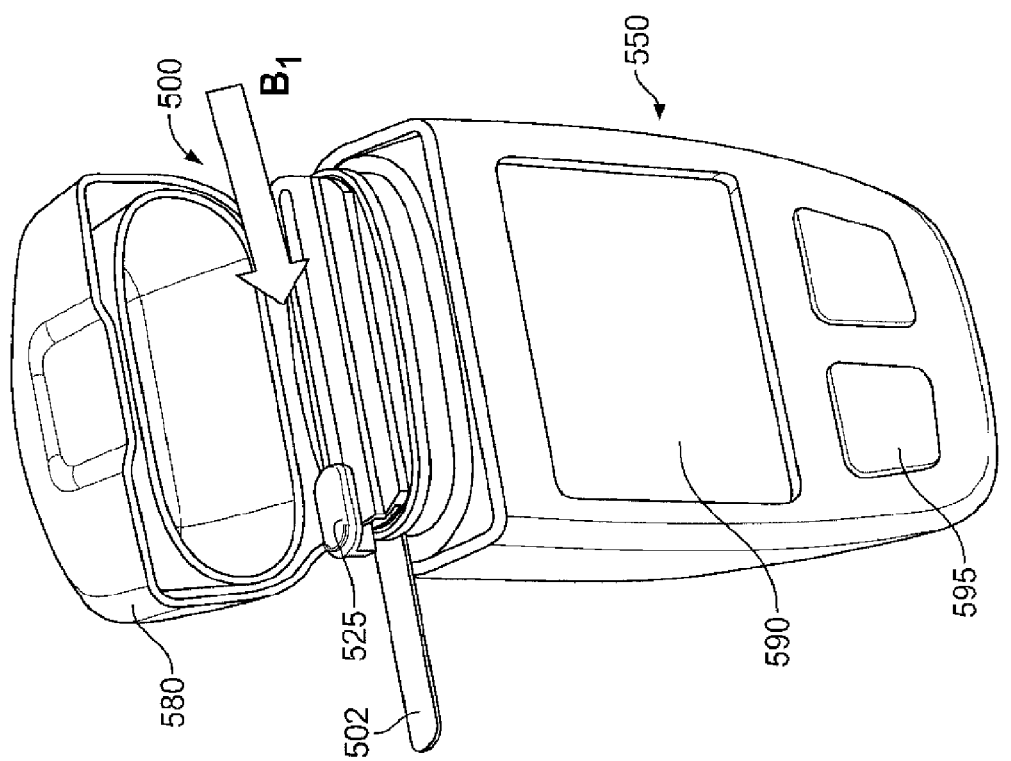

FIG. 4A illustrates a second embodiment of a sensor cartridge 400 for storing a plurality of biosensors (not shown). Sensor cartridge 400 provides a sealed, substantially moisture-impervious environment for storing the plurality of biosensors. Cartridge 400 may be made of a rigid or semi-rigid material such as plastic that forms a frame. Common materials used to form cartridge 400 include thermoplastics. In this embodiment, cartridge 400 has an overall oval shape, although any desired shape can be used. Unlike cartridge 100, sensor cartridge 400 does not include a bottom opening, and thus biosensors disposed within sensor cartridge 400 are completely sealed from the atmosphere until biosensors are ejected. Cartridge 400 can therefore be used as a stand-alone cartridge packaged for individual use or cartridge 400 can be directly incorporated into a meter. When cartridge 400 is utilized as a stand-alone cartridge for individual consumer use, cartridge 400 allows an individual user to store and dispense biosensors. The size and shape of cartridge 400 permit a user to hold cartridge 400 in the palm the user's hand, as well as place cartridge 400 in the user's pocket. Cartridge 400 also permits a user to deposit a fluid sample onto the biosensor and place the biosensor into a meter without having to physically contact or touch a biosensor stored therein. Of course, if cartridge 400 is incorporated into the design of a test sensor (as will be discussed in embodiments herein), a user is able to physically pull the biosensor from cartridge 400 and place it into a test meter.

According to one embodiment, the plurality of biosensors is stacked, substantially one on top of the next. Each biosensor has a first edge 413 and a second edge 415, the first and second edges 413,415 being aligned with one another. Sensor cartridge 400 includes a can 430 disposed within a case 440. Sensor cartridge 400 is different from cartridge 100 in that it includes cap portion 410 having an integrated picker 425. Picker 425 may be configured to horizontally slide along cap portion 410 on a track. The edge of picker 425 may also be configured to couple or engage a biosensor to push the biosensor out of cartridge 400, as will be more fully explained.

FIGS. 4B-4C illustrate sensor cartridge 400 without case 400 (and with FIG. 4B not including biosensors). As best seen in FIG. 4C, a plurality of biosensors 412 are supported in can 430 by a base 452 biased toward the top 458 of sensor cartridge 400. Spring 470 is capable of driving the base 452 and biosensors to the top of cartridge 400 near picker 425. Alternative mechanisms may also be used to urge base 452 and/or biosensors 412 to the top of cartridge 400. For example, a pawl and ratcheting mechanism or metering device may be incorporated into the cartridge to provide upward movement of biosensors 412. Similarly, a dispensing system similar to the design disclosed in copending application U.S. application Ser. No. 13/730,436 filed on Dec. 28, 2012 and entitled Multistrip Cartridge may be utilized, the disclosure of which is incorporated herein by reference. Sensor cartridge 400 may further include a protective lid (not shown) disposed over cap portion 410 to protect the picker 425 from damage during storage or shipment.

FIGS. 4C and 4D illustrate a cross-sectional schematic view of can 430 with biosensors 412 stacked therein. Strip picker 425 is shown adjacent a first biosensor 412A, which is positioned at the top of the stack of biosensors 412. Strip picker 425 includes a finger 460 with an edge 462 having a height $H_B$ that is slightly smaller than the height $H_B$ of biosensor 412A. Put another way, height $H_H$ of biosensor 412A should be slightly greater than a height $H_F$ of finger 460. For example, if biosensor 412A has a height $H_B$ of 0.43 mm, height $H_F$ of finger 460 can be slightly less than 0.43 mm, such as 0.35 mm. It is to be appreciated that this embodiment provides only one example and that any size test strip may be utilized. In such alternative embodiments, biosensors will also have a height $H_F$ of finger 460 that is slightly less than the height $H_B$ of the biosensor. Although not limited to such ranges, such alternative embodiments may have a height $H_B$ ranging from 0.30 mm to 0.50 mm and the finger 460 can have a corresponding height $H_F$ ranging from 0.29 mm to 0.49 mm.

In use, the user would open or remove the lid to expose the picker 425. Picker 425 may be horizontally slid in direction X so that edge 462 of finger 460 engages edge 413 of test strip 412A. As picker 425 is slid in the horizontal direction X, biosensor 412 moves laterally across the top of the remaining biosensors 412 in the stack. Picker 425 moves first edge 413 of biosensor 412 into exit channel 482 and into opening 484 of can 430, such that first and second edges 413,415 of biosensor 412A are no longer aligned or collinear with the first and second edges 413,415 of the remaining biosensors 412A in the stack. Once picker travels the length of top track 411 (FIG. 4A), first edge 413 of biosensor is free or cantilevered. Second edge 415 of biosensor 412A remains within exit channel 482, allowing a user to deposit a fluid sample onto biosensor 412. Even though the picker consistently pushes only one sensor, friction can also drag an adjacent sensor forward. It is the height of the opening 484 which restricts all but one sensor from being pushed forward and out of the cartridge opening. A user may then move cartridge 400 toward a test meter (not shown) and place biosensor 412A directly into a test meter without being required to touch, handle, or contact biosensor 412A. The user may then return picker 425 to its original position and close the lid, storing sensor cartridge 400 for future use.

FIGS. 5A-D illustrate a third embodiment of the device including a sensor cartridge 500 disposed within a blood glucose monitor. Sensor cartridge 500 is similar to sensor cartridge 400 except that it may be used with blood glucose monitor 550. Blood glucose monitor 550 may include a cavity "C" in the shape of cartridge 500 housed within the monitor, and an acceptance slot 560 for accepting a biosensor 502 into the interior of the monitor. In at least some examples, each sensor cartridge 500 includes a coding on the bottom of the cartridge. This coding may be read by the blood glucose monitor 550 to determine the brand, type or kind of biosensor being used. Due to variation in biosensor manufacturing, this coding may allow blood glucose monitor to be automatically calibrated based on the biosensor being used. In other embodiments, each individual biosensor includes a coding for calibration that is read by the blood glucose monitor 500. Blood glucose monitor 550 may also include an LCD display 590 and a plurality of functional buttons (e.g., power, display settings, biosensor selection, etc.). The blood glucose monitor 550 further includes buttons 595, capable of toggling between modes or adjusting for various test strips, for changing settings of display 590 such as contrast and/or color, for powering the device on or off, or for checking to see whether the device is functioning properly, such as checking the battery level.

In use, the user may open lid 580 by flipping lid 580 over hinge 578 at the top of the blood glucose monitor 550 to reveal slide picker 525. The user may then slide picker 525 across the top of the meter in the direction of arrow "B1" to receive a biosensor 502 from cartridge 500. A blood sample may be placed on biosensor 502 and the sampling biosensor may be introduced into receiving slot 502 in order to obtain a measurement relating to blood glucose on display 590.

Figure 6A:
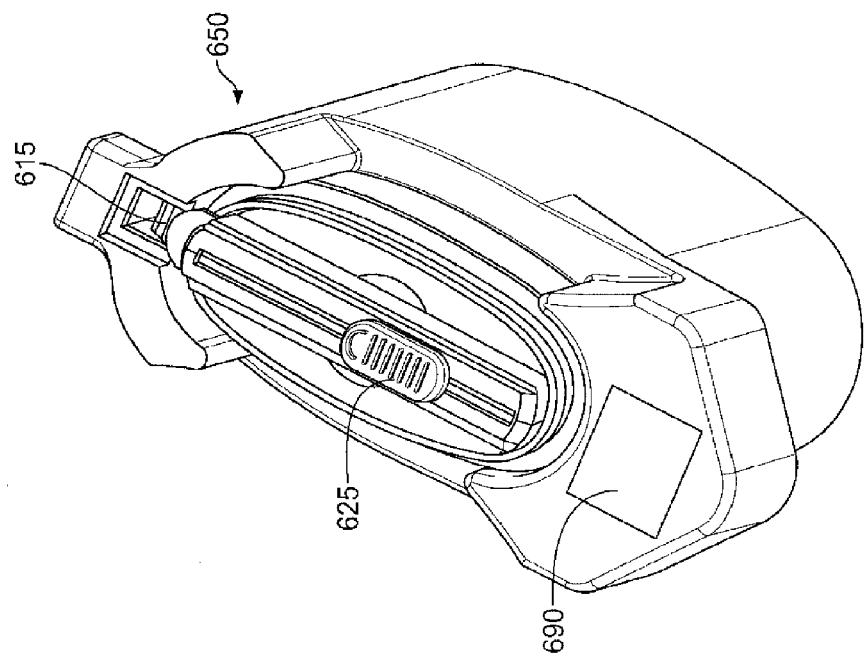
Figure 6B:
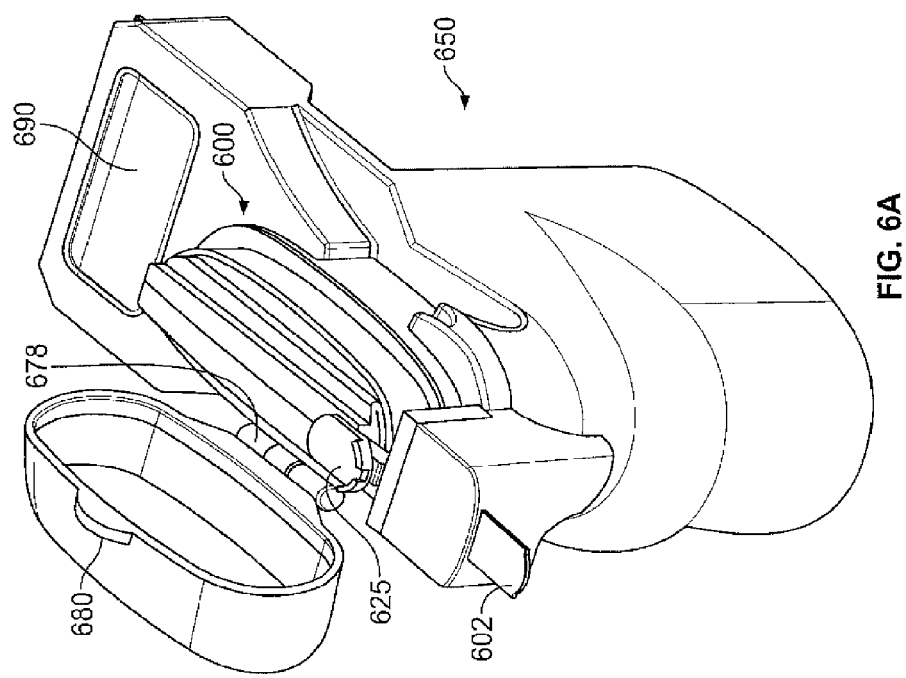

FIGS. 6A-C illustrate yet another embodiment of a blood glucose monitor 650 having a sensor cartridge 600. Sensor cartridge 600 may be similar to any of the sensor cartridges discussed above and may include a picker 625 for actuating a biosensor 602. An optional lid 680 may also be included to protect picker 625 and the top of the assembly.

As seen in FIG. 6B, blood glucose monitor 650 may include electrodes 615 for contacting biosensor 602 and measuring relevant blood glucose information. In contrast to the embodiment described above with reference to FIGS. 5A-5D, blood glucose monitor 650 may be used without the user touching biosensors 602. Instead, the user may open lid 680 over hinge 678 and slide picker 625 in the direction of arrow "B2" to slide out a biosensor 602. A blood sample may be placed on biosensor 602 and slid back into blood glucose monitor 650 using picker 625 in a reverse direction opposite arrow "B2". Electrodes 615 may contact biosensor 602 and a measurement may be obtained from display 690. Thus, the user does not need to touch biosensor 602, which leads to more accurate results.

In at least some examples of this embodiment, lid 680 and other portions of the device may be separable and coupleable to either edge of the blood glucose monitor 650 or the sensor cartridge 600 such that the device may be used by both right-handed and left-handed users. In such an embodiment, two hinges 678 may be disposed on either side of the sensor cartridge 600 such that lid 680 may be coupled and pivoted over either hinge. The symmetry of the device allows for simple conversion between right-handed and left-handed configurations.

Figure 7C:
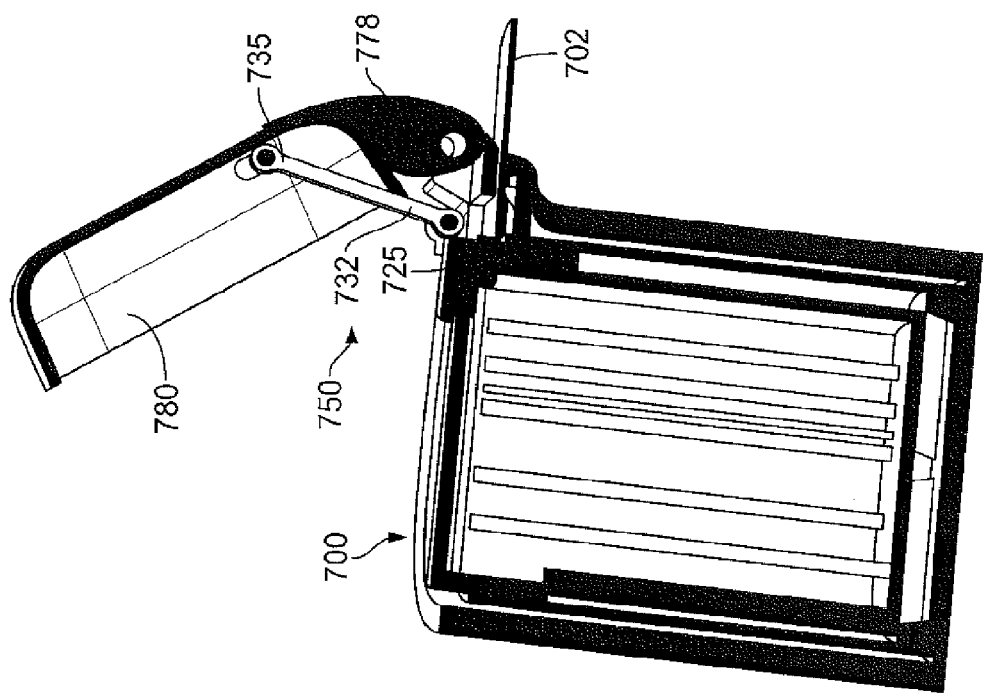
Figure 7B:
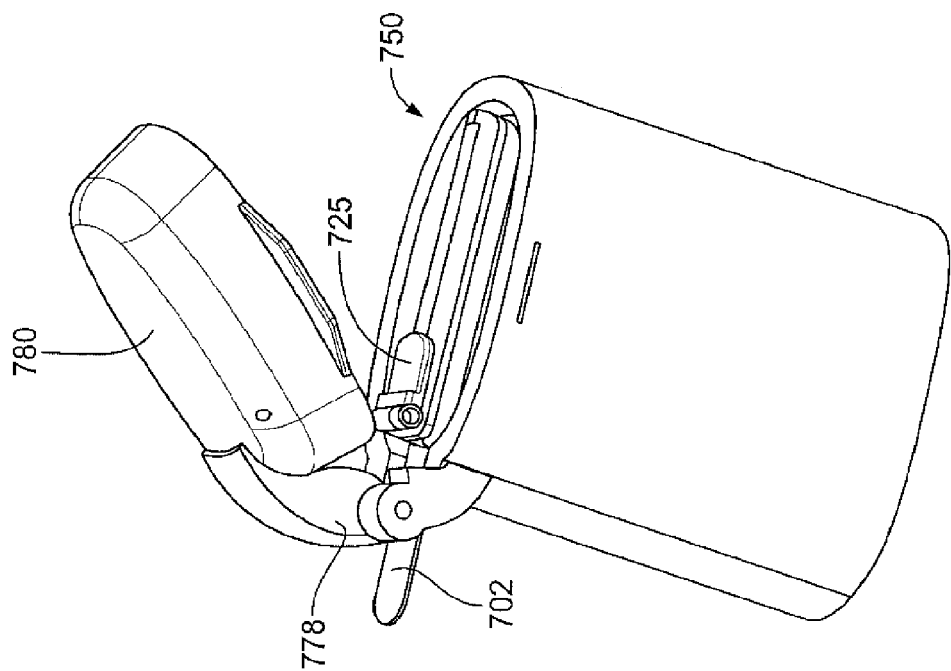

In another embodiment, shown in FIGS. 7A-C, a semi-automated blood glucose monitor 750 is shown. Blood glucose monitor 750 may be similar to blood glucose monitor 650 except for the configuration of lid 780. In this example, lid 780 is connected at the back of blood glucose monitor 750 at hinge 778 and may be coupleable to sled 725 on sensor cartridge 700 via ribbon 732 such that opening of lid 780 also functions to pull sled 125 to deploy a biosensor 702 as shown in FIGS. 7B and 7C. In at least some examples, lid 780 may be coupleable to sled 725 via arm 735. As seen in FIGS. 7B and 7C, by opening lid 780, biosensor 702 is pulled out and placed in a position to deposit a blood sample on biosensor 702. Closing lid 780 moves sled 725 back into its original position.

FIGS. 8A-C, 9A-C and 10A-C illustrate several variations of the embodiments disclosed herein. FIGS. 8A-C illustrates a pass-through and re-orient embodiment of a sensor cartridge 800. Sensor cartridge 800 may be similar to sensor cartridge 400 of FIGS. 4A and 4B and include any of the components described above with respect to that embodiment. For example, as shown in FIG. 8A, sensor cartridge 800 includes a case 860 coupled to a lid 880 having cutout 881 via hinge 878. Sensor cartridge further includes a picker 825 and a rotating block 806. To use sensor cartridge 800, the user may open lid 880 by flipping it over hinge 878 to expose picker 825. A biosensor 802 may be advanced using picker 825 and lid 880 may be closed. Rotating block 806 may be coupled to lid 880 such that closing lid 880 swivels rotating block 806 in the direction of arrow "R" and biosensor 802 is exposed through cutout 881 of lid 880. Thus, biosensor 802 is reoriented to a second position, which may be easier for some users to grasp.

In FIGS. 9A-C an embodiment having an automatic pass through is illustrated which includes a spring-loaded pusher. The lid 980 is pushed up as seen in FIG. 9A and a ribbon 932 in the form of a spring pusher connects the lid 980 to a sled 925. Closing of the lid 980 causes the spring pusher to advance a biosensor 902 through the front of the device. This concept is similar to that shown in FIGS. 7A-C, except that the biosensor 902 is being passed to the front of the device 900 opposite the hinge 932 and the biosensor 902 is being deployed when the lid 980 is closed.

Figure 10A:
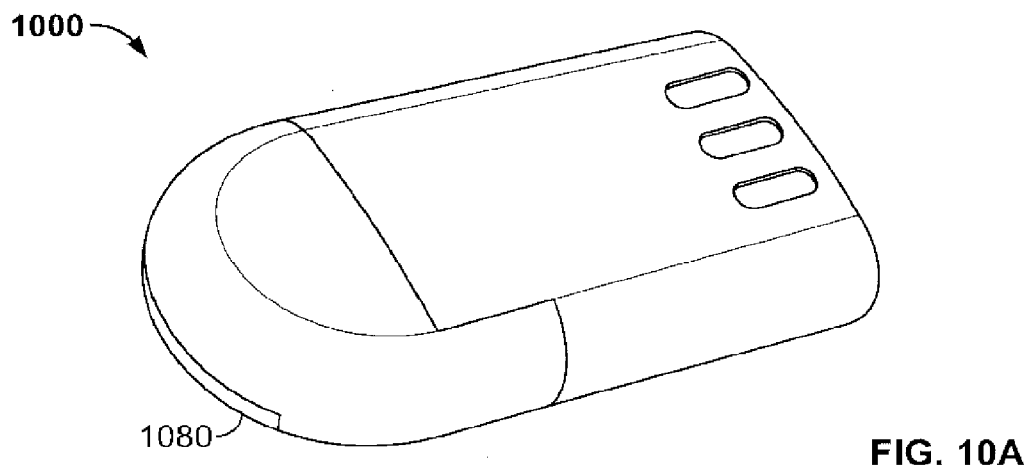
FIGS. 10A-C are perspective views of a blood glucose monitor and a sensor cartridge disposed within the monitor according to a sixth embodiment of the present invention.
Figure 10B:
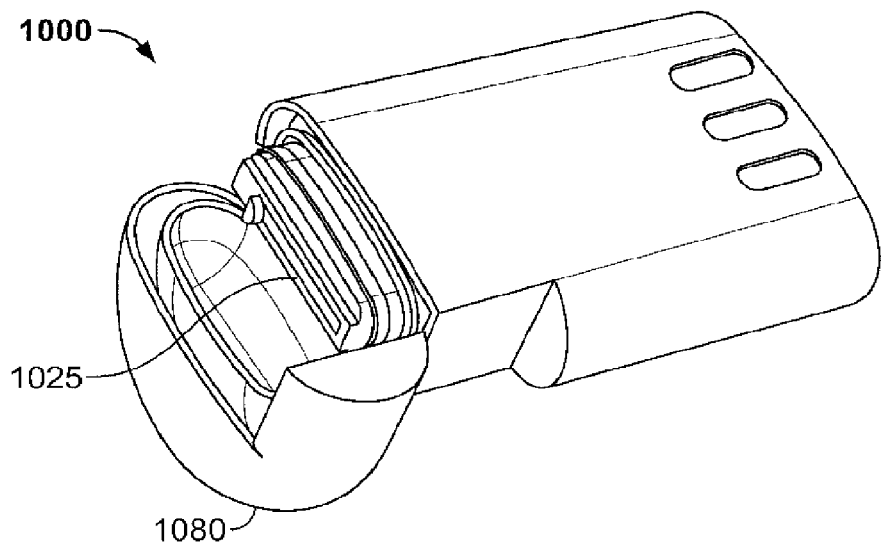
Figure 10C:
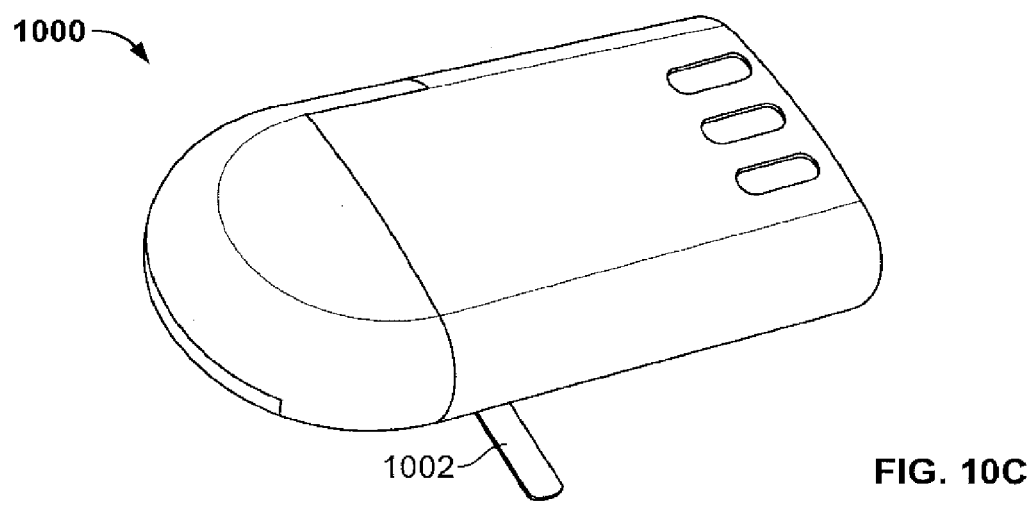

FIGS. 10A-C illustrate a pass through and reorient embodiment similar to that shown in FIGS. 8A-C. In this embodiment, sensor cartridge 1000 includes a hinged lid 1080 that opens as shown in FIG. 10B. When the lid 1080 is being closed, a picker (not shown) advances a biosensor 1002 and reorients the biosensor 1002 using a rotating block (also not shown) so that it is advanced toward the user. Thus, using the rotating blocks described above, a biosensor may be reoriented and passed to the user at various angles and from various sides of the sensor cartridge 1000. In addition to the embodiments, described several features may be added to any of the sensor cartridges or meters described to facilitate usage and increase reliability of the product. For example, in using a sensor cartridge or meter, a failure may occur when a slider or picker is partially cycled. Specifically, the user may advance a slider to engage a biosensor and advance it partially toward outside the device. If, however, the user stops the slider before completing the forward stroke and returns it to the home position, the slider may then engage a second biosensor. In some embodiments, the device may be configured to deliver a single biosensor at a time. Thus, when two biosensors attempt to exit the cartridge slot simultaneously, the slider may become jammed from moving forward. Returning the slider to the home position may exacerbate the problem by engaging additional biosensors.

Additionally, a single "dog-earred," bent, frayed or damaged biosensor may jam within the cartridge slot. Once a single bios sensor becomes jammed in a slot, others biosensors may become jammed as well. To address jamming of the biosensors, several features are described below. These features may be combined or used in conjunction with any of the embodiments described above.

Figure 11A:
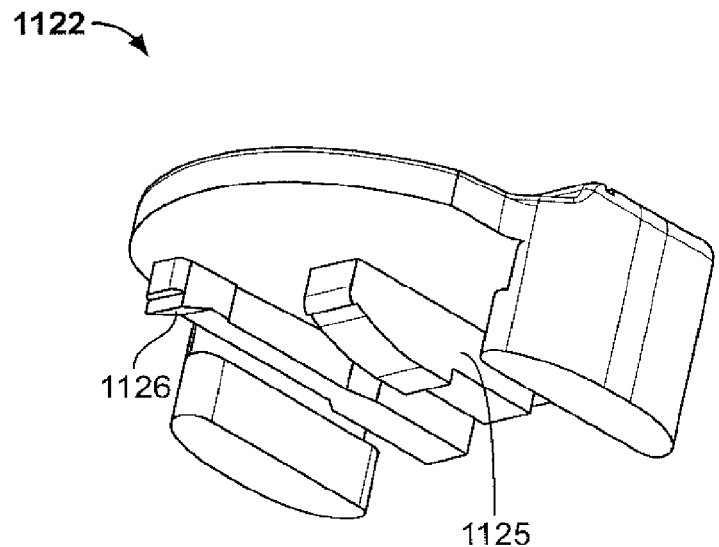
FIGS. 11A and 11B are perspective views of a slider and associated can according to another embodiment of the present invention.
Figure 11B:
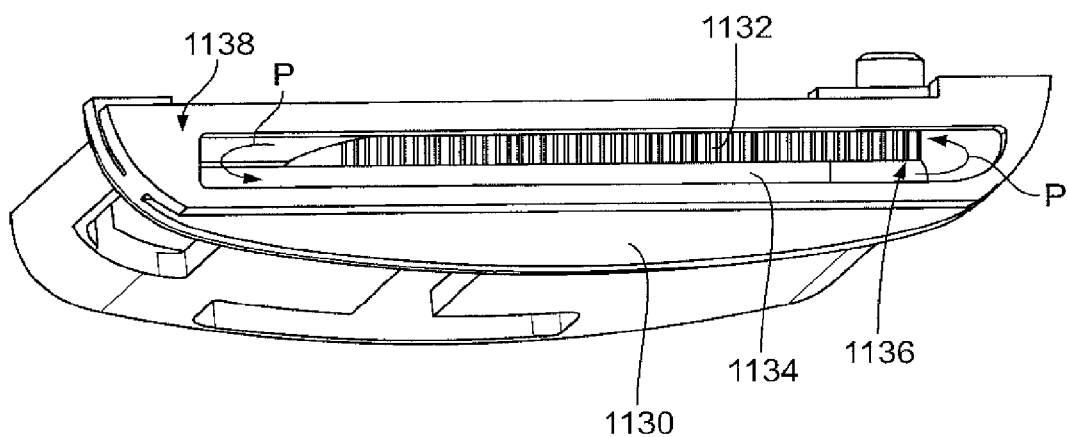

FIG. 11A is a perspective view of a slider 1122 having a picker 1125 for engaging a biosensor and a pawl 1126. Picker 1125 may be formed in any of the configurations shown above. Pawl 1126 may be formed of a laterally flexible ratchet material. The addition of a pawl 1126 on the underside of the slider 1122 (e.g., the same side as the picker), may alleviate the problem of jamming when used in conjunction with the can 1130 of FIG. 11B. Can 1130 includes ratchet teeth 1132 that extend from a home position 1136 to an end position 1138, upon which pawl 1126 may travel. Can 1130 further includes a smooth track 1134 that extends parallel to the ratchet teeth 1132.

In use, pawl 1126 of slider 1122 may slide forward over ratchet teeth 1132 of can 1130. Pawl 1126 and ratchet teeth 1132 may be configured such that the pawl 1126 can only travel over ratchet teeth 1132 in the forward direction and not in the reverse direction. Once pawl 1126 has traveled forward over the ratchet teeth, it may be urged to drop down to smooth track 1134 via, in some cases, track 1132 tapering to urge the pawl to track 1134 at end position 1138 in the direction of left arrow "P". Pawl 1126 and, thus slider 1122, may travel back over smooth track 1134 from end position 1138 to home position 1136. In this manner, slider 1122 must complete a full stroke over ratchet teeth 1132 before returning to the home position, resulting in less jamming of the biosensors.

Figure 11C:
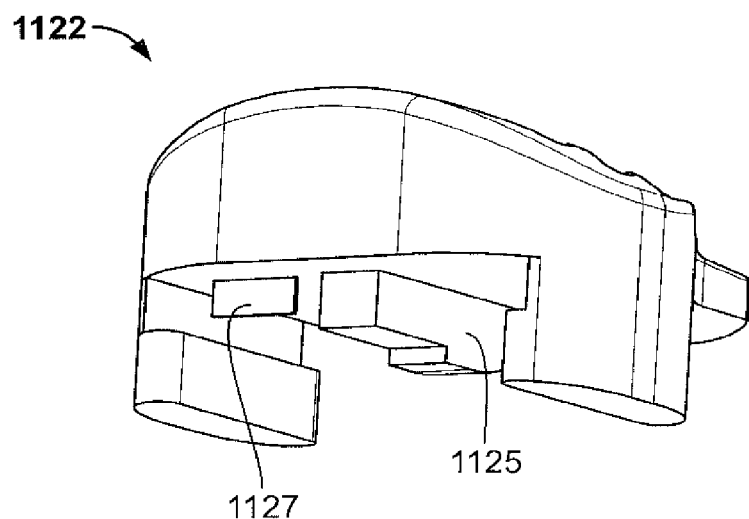
FIGS. 11C and 11D are perspective views of a slider and associated can according to another embodiment of the present invention.
Figure 11D:
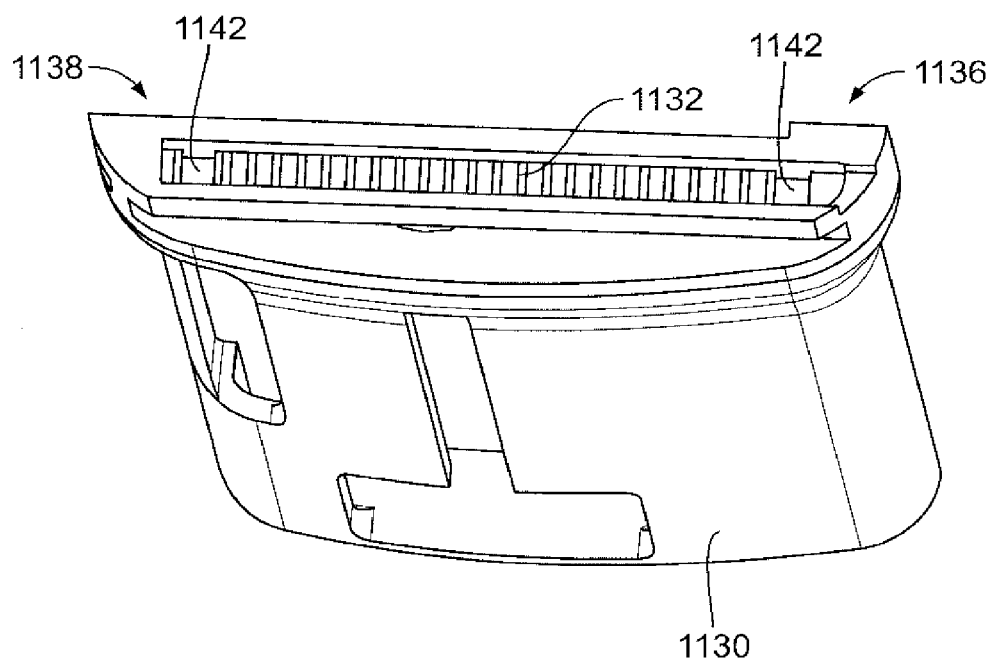

A variation of this embodiment is shown in FIGS. 11C and 11D. Similar to the above embodiment of FIGS. 11A-B, this embodiment includes a slider 1122 having a picker 1125. Instead of a pawl 1126 at the back end of the slider 1122, the slider of FIG. 11C includes a flexible tab stop 1127. Tab stop 1127 is guided over ratchet teeth 1132 of can 1130, shown in FIG. 11D, which includes a pair of pockets 1142 at the home position 1136 and the end position 1138 instead of a smooth track. Pocket 1142 may form a clearance that is large enough to allow reversal of the orientation of flexible tab stop 1127.

Tab stop 1127 may slide over ratchet teeth 1132 in a forward direction from home position 1136 to end position 1138 but may be incapable of moving the reverse direction. Once tab stop 1127 reaches pocket 1142 at the end position 1138, it may reverse orientation within pocket 1142 and travel back over ratchet teeth 1132. Thus, in this manner, tab stop 1127 is reversible only within pockets 1142 and slider 1122 only switches directions of travel while intra cycle (e.g., at the ends of the ratchet teeth 1132 at pockets 1142). Thus, this variation also compelling slider 1122 to complete a full stroke over ratchet teeth 1132 before returning to the home position, resulting in less jamming of the biosensors.

Figure 12A:
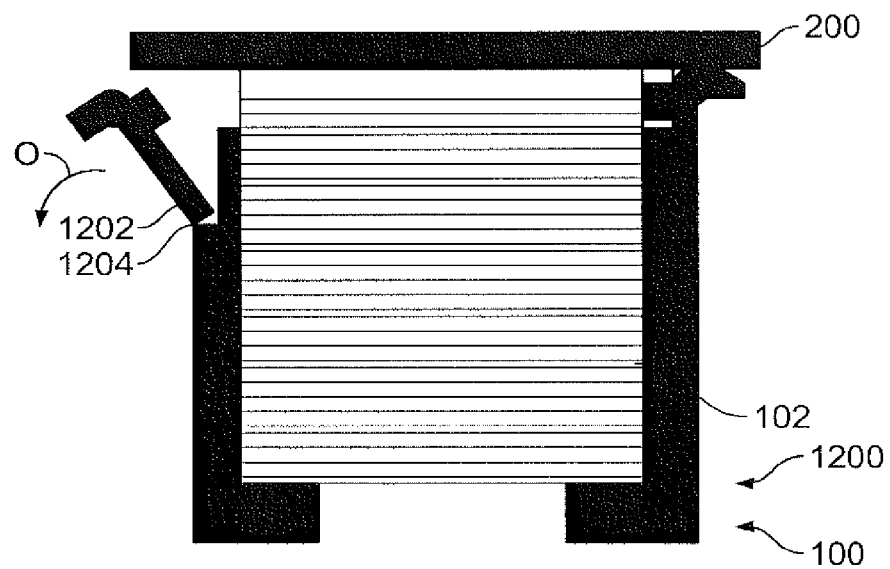
FIG. 12A is a schematic cross-sectional view of a replaceable cartridge having an anti-jamming feature according to one embodiment of the present invention.

FIG. 12A is a schematic cross-sectional view of a replaceable cartridge similar to FIG. 3B but having an anti-jamming feature. Sensor cartridge 100 may be loaded in a meter housing 200. Meter housing 200 may include a taper fitting 204 that will contact sealing flange 106. During loading a taper fitting 204 in the meter housing 200 engages sensor cartridge 100 and deforms it in such a way as to allow biosensors 102 to move freely. Sensor cartridge 100 may further include a deflecting portion 1202 attached at hinge 1204. Deflecting portion 1202 may rotate about hinge 1204 in the direction of arrow "O" to open and provide access to the interior of sensor cartridge 100. Thus, when a deformed biosensor or multiple biosensors 102 do not exit smoothly, the flexible deflecting portion 1202 may create a temporary allowance of more than one biosensor to clear the jam.

Figure 12B:
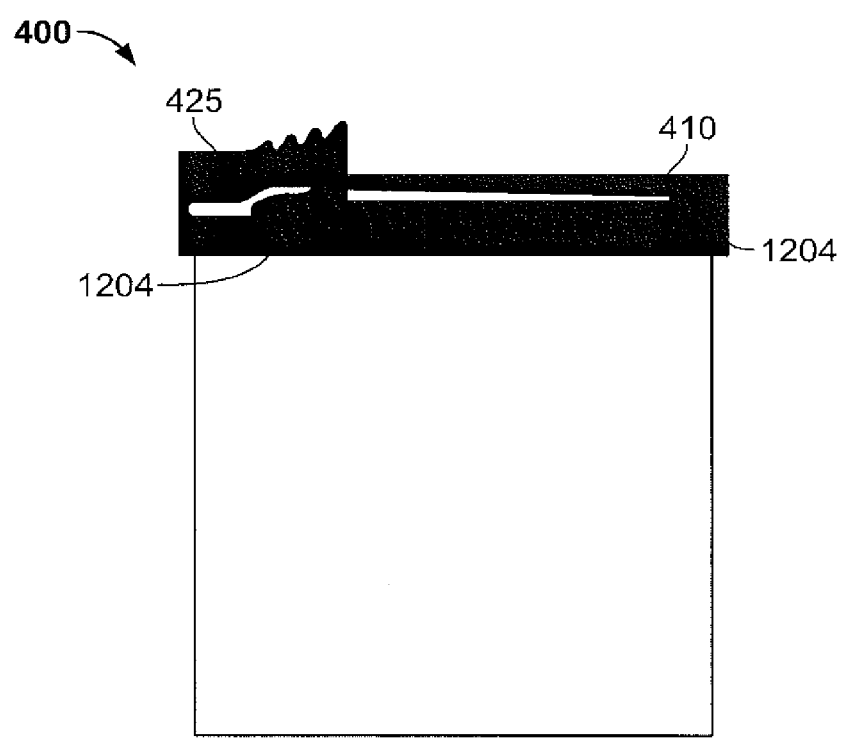
FIG. 12B is a schematic side view of a replaceable cartridge having a feedback feature according to one embodiment of the present invention.

FIG. 12B is a schematic side view of a replaceable cartridge 400 similar to that described in FIG. 4B but having a feedback feature 1204. Feedback feature 1204 may be in the form of depressions formed at positions beneath picker 425 and cap portion 410 and may provide a snapping sound or tactile feedback to the user about the location of picker 425. Thus, the user may become aware that the picker 425 has reached the end of the forward stroke or backward stroke, reducing the risk of biosensor jamming. In addition to depressions, it will be understood that feedback feature 1204 may also include ribs, bumps, recesses, or any other feature capable of providing tactile feedback while allowing picker 425 to travel smoothly across the track as described in the above embodiments. It will be understood that replaceable cartridge 400 may include one, two, three, four or more feedback features 1204 and that the feedback features may include any of the combinations described above.

In addition to these features, the lid of the device may further be modified to prevent jamming and partially excised biosensors. Specifically, if a slider or picker does not complete a full forward stroke, a partially excised biosensor may remain in the cartridge. Jammed or partially excised biosensors may allow humidity into the device, thereby damaging the biosensors.

FIGS. 13A and 13B are schematic cross-sectional views of a lid 1380 according to one embodiment of the present invention. As seen in these figures, lid 1380 may include a ridge 1382 along the length of the lid, and having a small cavity 1384 for accepting a picker. Ridge 1382 prevents lid 1380 from closing on the sensor cartridge unless the picker is returned to an end (e.g., home position) within cavity 1384. Thus ridge 1382 may disallow closure of a lid 1380 until the picker is returned to the home position. This feature may be used alone or in combination with any of the features disclosed above.

A disposal area for used biosensors may also be incorporated into any of the embodiments shown above. FIGS. 14A and 14B are back end and schematic cross-sectional views of one such cartridge. Replaceable cartridge 1400 includes a disposal compartment 1484 in a lid 1480. Disposal compartment 1484 may be in communication with ambient air via disposal slot 1482 in the back of the sensor cartridge 1400. Lid 1480 may be capable of opening over hinge 1478 to expose a picker or slider as described above. The user may close lid 1480 after using the biosensor and dispose of the contaminated biosensor through disposal slot 1482 into disposal compartment 1484. Disposal compartment 1484 may be sealed off from any of the other components of the device. Additionally, disposal slot 1482 may include a closing flap 1486 to prevent contaminated biosensors from falling out of the disposal compartment. When the disposal compartment 1484 is full or the device is out of biosensors, the user may dispose of the entire device with the contaminated biosensors.

In addition to ratchet teeth, and lids with ridges, features may be added to automatically retract a picker to the home position. FIGS. 15A-C are schematic illustrations of a replaceable cartridge 1500 having a retraction spring 1510 coupled to picker 1525. Retraction spring 1510 may include a constant force spring 1525 to urge picker 1525 to the home position. Thus, a user may actuate picker 1525 to engage a biosensor and push the picker against the spring force. Once the user releases the picker 1525, retraction spring 1510 may force picker 1525 to return to the home position. In this way, the likelihood of engaging multiple strips may be decreased.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

What is claimed is:
1. A blood glucose monitor comprising:
   a replaceable sensor cartridge comprising:
      a frame having at least two walls defining a chamber for accepting a plurality of biosensors, the frame having a bottom portion defining an opening and at least one sealing flange, the frame further including a desiccant material capable of reducing humidity within the frame, wherein the frame is dimensioned such that an interference fit constrains the plurality of biosensors;

a can capable of receiving the replaceable sensor cartridge;
an upper spring disposed between the frame and the can;
a case for housing the can and sealing the frame;
a lower spring disposed between the can and the case; and
a meter housing for sealing an upper portion of the frame.

2. The blood glucose monitor of claim 1, wherein the upper spring is received in the opening in the bottom portion of the frame.

3. The blood glucose monitor of claim 1, wherein the lower spring has a spring force higher than that of the upper spring.

4. The blood glucose monitor of claim 1, wherein the meter housing and the replaceable sensor cartridge define a segregating slot there between to allow deployment of only a single one of the plurality of biosensors.

5. The blood glucose monitor of claim 4, further comprising a pusher to advance a single one of the plurality of biosensors through the segregating slot.

6. The blood glucose monitor of claim 1, further comprising a pusher to advance a single one of the plurality of biosensors.

7. A replaceable sensor cartridge comprising:
a frame having a desiccant material capable of reducing humidity within the frame and configured to house a plurality of biosensors; and
a strip picker configured and arranged to slide along a top portion of the frame in a forward stroke to deploy a top biosensor from the plurality of biosensors and in a reverse stroke to return the strip picker to a home position, the strip picker including a flexible tab stop for providing a ratchet action along the top portion of the frame such that the strip picker cannot return to the home position until a full forward stroke is completed.

8. The replaceable sensor cartridge of claim 7, wherein the frame includes a plurality of ratchet teeth and a pocket at each end of the plurality of ratchet teeth, the frame configured to mate with the flexible tab stop and to reverse movement of the strip picker only in response to completion of a full forward or reverse stroke.

9. The replaceable sensor cartridge of claim 7, wherein the strip picker is configured to deploy a first edge of the top biosensor from the plurality of biosensors through an exit channel of the frame and leave a second opposite edge of the top biosensor within the exit channel.

10. The replaceable sensor cartridge of claim 7, further comprising an anti-jamming feedback feature.

11. The replaceable sensor cartridge of claim 10, wherein the anti-jamming feedback feature provides tactile feedback when the strip picker is at an end of the forward or reverse stroke.

12. A blood glucose monitor comprising:
the replaceable sensor cartridge of claim 7; and
a rotating block configured to reorient a deployed top sensor from a first position to a second position.

13. The blood glucose monitor of claim 12, further comprising a lid for covering the top portion of the frame of the replaceable sensor cartridge, the lid coupled to the rotating block and having a cutout configured to allow reorientation of the deployed top sensor from the first position to the second position.

14. A blood glucose monitor comprising:
a replaceable sensor cartridge comprising:
a frame having a desiccant material capable of reducing humidity within the frame and configured to house a plurality of biosensors, and
a strip picker configured and arranged to slide along a top portion of the frame in a forward stroke to deploy a top biosensor from the plurality of biosensors and in a reverse stroke to return the strip picker to a home position, the strip picker providing a ratchet action along the top portion of the frame such that the strip picker cannot return to the home position until a full forward stroke is completed; and
electrodes for contacting one of the plurality of biosensors; wherein:
the strip picker is configured and arranged to slide along a top portion of the frame in a reverse stroke to return a deployed top biosensor to the home position such that the deployed top biosensor is in contact with the electrodes.

15. The blood glucose monitor of claim 14, wherein the strip picker of the replaceable sensor cartridge includes a flexible pawl for providing the ratchet action.

16. The replaceable sensor cartridge of claim 15, wherein the frame includes a plurality of ratchet teeth and a parallel smooth track, the frame configured to mate with the flexible pawl of the strip picker to allow the forward stroke along the ratchet teeth and to guide the reverse stroke along the smooth track only in response to completion of the full forward stroke.

17. A blood glucose monitor comprising:
a replaceable sensor cartridge comprising:
a frame having a desiccant material capable of reducing humidity within the frame and configured to house a plurality of biosensors, and
a strip picker configured and arranged to slide along a top portion of the frame in a forward stroke to deploy a top biosensor from the plurality of biosensors and in a reverse stroke to return the strip picker to a home position, the strip picker providing a ratchet action along the top portion of the frame such that the strip picker cannot return to the home position until a full forward stroke is completed;
a first hinge disposed on one side of the replaceable cartridge and a second hinge disposed on an opposite side of the replaceable cartridge; and
a lid coupleable to either the first hinge or the second hinge for pivoting over either the first hinge or the second hinge.

18. The blood glucose monitor of claim 17, wherein the strip picker of the replaceable sensor cartridge includes a flexible pawl for providing the ratchet action.

19. A replaceable sensor cartridge comprising:
a frame having a desiccant material capable of reducing humidity within the frame and configured to house a plurality of biosensors;
a strip picker configured and arranged to slide along a top portion of the frame in a forward stroke to deploy a top biosensor from the plurality of biosensors and in a reverse stroke to return the strip picker to a home position, the strip picker providing a ratchet action along the top portion of the frame such that the strip picker cannot return to the home position until a full forward stroke is completed; and
an anti-jamming feedback feature that provides a snapping sound when the strip picker is at an end of the forward or reverse stroke.

20. A replaceable sensor cartridge comprising:
a frame having a desiccant material capable of reducing humidity within the frame and configured to house a plurality of biosensors;

a strip picker configured and arranged to slide along a top portion of the frame in a forward stroke to deploy a top biosensor from the plurality of biosensors and in a reverse stroke to return the strip picker to a home position, the strip picker providing a ratchet action along the top portion of the frame such that the strip picker cannot return to the home position until a full forward stroke is completed; and an anti-jamming feedback feature that includes a depression disposed on the frame.

* * * * *